US008805703B2

(12) United States Patent
Martin et al.

(10) Patent No.: US 8,805,703 B2
(45) Date of Patent: Aug. 12, 2014

(54) GENERATION AND DISSEMINATION OF AUTOMATICALLY PRE-POPULATED CLINICAL NOTES

(75) Inventors: Neil A. Martin, Encino, CA (US); Farzad D. Buxey, Marina del Rey, CA (US); Valeriy I. Nenov, Los Angeles, CA (US); Xiao Hu, Los Angeles, CA (US); Vesselin Zlatev, Aliso Viejo, CA (US)

(73) Assignees: The Regents of the University of California, Oakland, CA (US); Vesselin Zlatev, Aliso Viego, CA (US)

( * ) Notice: Subject to any disclaimer, the term of this patent is extended or adjusted under 35 U.S.C. 154(b) by 175 days.

(21) Appl. No.: 12/247,987

(22) Filed: Oct. 8, 2008

(65) Prior Publication Data

US 2009/0182580 A1    Jul. 16, 2009

Related U.S. Application Data

(60) Provisional application No. 60/978,396, filed on Oct. 8, 2007, provisional application No. 61/030,988, filed on Feb. 24, 2008.

(51) Int. Cl.
*G06Q 30/00* (2012.01)
*G06Q 50/00* (2012.01)

(52) U.S. Cl.
USPC ................................. 705/3; 705/2; 707/770

(58) Field of Classification Search
USPC .............. 705/2, 3; 600/300, 301; 707/10, 770
See application file for complete search history.

(56) References Cited

U.S. PATENT DOCUMENTS

| 5,553,609 A | 9/1996 | Chen et al. |
| 5,713,350 A | 2/1998 | Yokota et al. |
| 5,823,948 A | 10/1998 | Ross, Jr. et al. |
| 5,827,180 A | 10/1998 | Goodman |
| 5,832,488 A | 11/1998 | Eberhardt |
| 5,867,821 A | 2/1999 | Ballantyne et al. |
| 5,924,074 A | 7/1999 | Evans |
| 5,950,207 A | 9/1999 | Mortimore et al. |
| 5,960,403 A | 9/1999 | Brown |
| 6,049,794 A | 4/2000 | Jacobs et al. |

(Continued)

FOREIGN PATENT DOCUMENTS

| WO | 2005088506 A1 | 9/2005 |
| WO | 2006093544 A2 | 9/2006 |

OTHER PUBLICATIONS

European Search Report; Application No. EP 08 83 7951; Issued: Dec. 5, 2011; Mailing Date: Dec. 13, 2011; 9 pages.

*Primary Examiner* — Hiep V Nguyen
*Assistant Examiner* — Teresa Woods
(74) *Attorney, Agent, or Firm* — St. Onge Steward Johnston & Reens LLC

(57) ABSTRACT

Some embodiments provide a system and method for automatedly aggregating medically related data and disseminating different sets of the aggregated data to two or more different members of a medical care provider. Some embodiments automatedly and intelligently disseminate the aggregated data such that the data that is written once to the data storage solution is usable for a multitude of purposes within the functions of the medical care provider. Some embodiments intelligently disseminate the aggregated data by disseminating only relevant sub-components of the data to different members of the medical care provider based on the needs of the members such that different members receive different subsets of the data.

29 Claims, 14 Drawing Sheets

(56) References Cited

U.S. PATENT DOCUMENTS

| | | |
|---|---|---|
| 6,182,029 B1 | 1/2001 | Friedman |
| 6,226,620 B1 | 5/2001 | Oon |
| 6,246,992 B1 | 6/2001 | Brown |
| 6,283,761 B1 | 9/2001 | Joao |
| 6,375,614 B1 | 4/2002 | Braun et al. |
| 6,523,009 B1 | 2/2003 | Wilkins |
| 6,611,846 B1 | 8/2003 | Stoodley |
| 7,165,221 B2 | 1/2007 | Monteleone et al. |
| 7,424,679 B1 | 9/2008 | Lamer et al. |
| 7,647,320 B2* | 1/2010 | Mok et al. ............ 707/770 |
| 7,912,733 B2* | 3/2011 | Clements et al. ............ 705/2 |
| 2002/0194029 A1 | 12/2002 | Guan et al. |
| 2003/0140044 A1 | 7/2003 | Mok et al. |
| 2003/0236683 A1* | 12/2003 | Henderson et al. ............ 705/2 |
| 2004/0073453 A1 | 4/2004 | Nenov et al. |
| 2004/0148194 A1* | 7/2004 | Wellons et al. ............ 705/2 |
| 2004/0186746 A1 | 9/2004 | Angst et al. |
| 2005/0149364 A1* | 7/2005 | Ombrellaro ............ 705/3 |
| 2006/0129434 A1 | 6/2006 | Smitherman et al. |
| 2006/0253303 A1 | 11/2006 | Brown |
| 2006/0271400 A1* | 11/2006 | Clements et al. ............ 705/2 |
| 2007/0005397 A1 | 1/2007 | Lee |
| 2007/0043596 A1 | 2/2007 | Donaldson et al. |
| 2008/0052115 A1 | 2/2008 | Spradley et al. |
| 2008/0077450 A1* | 3/2008 | Klippel ............ 705/4 |
| 2008/0249804 A1* | 10/2008 | Kim ............ 705/3 |

\* cited by examiner

GENERATION AND DISSEMINATION OF AUTOMATICALLY PRE-POPULATED CLINICAL NOTES

CLAIM OF BENEFIT TO PRIOR APPLICATION

This patent application claims the benefit of the U.S. Provisional Patent Application 60/978,396, filed Oct. 8, 2007, entitled "Generation and Dissemination of Automatically Pre-Populated Clinical Notes" and the U.S. Provisional Patent Application 61/030,988, filed Feb. 24, 2008, entitled "Generation and Dissemination of Automatically Pre-Populated Clinical Notes". The contents of the above mentioned applications, namely 60/978,396 and 61/030,988 are hereby incorporated by reference.

FIELD OF THE INVENTION

The invention relates to the field of health care. More specifically, the invention relates to systems and methods for generating and routing clinical notes and other medical related data.

BACKGROUND OF THE INVENTION

The quality of health care is constantly evolving and improving as new, less invasive surgical techniques, more effective medications, and better methods of treatment are constantly being discovered and invented. Improvements in health care have also occurred through better use and management of patient related medical information. By centrally storing patient information in a digital medium, medical personal are provided a readily accessible means of acquiring patient information. Such digital storage of patient information allows for fast searches to locate all previously entered patient information, sorting of the information to display only relevant information, and the ability to access the information from any location at any time so that doctors will be able to provide care even when absent from the hospital. Such examples are among the many benefits gained from the digitization and central storage of patient information within a medical environment.

Medical care providers have discovered that creating such digital medical databases often requires a dedicated set of resources to gather, transcribe, and manage the data. First, physicians, nurses, and other medical care providers generate clinical notes or rounding lists which include objective data acquired from monitors. These notes are composed by several individuals and different times throughout the day. As such, the notes often become disbursed in multiple places as each individual stores the data within separate files or as separate notes within the same file. The medical care members lose valuable time having to prepare and record such data. For instance, objective clinical information, such as the vital statistics displayed on a monitor (e.g., blood pressure monitors, heart rate monitors, etc.) attached to the patient, is data that has to be read from the monitor and manually transcribed to the notes at regular intervals. A clerical staff must then digitally transcribe the notes and rounding list information from the various medical care members into a digital database where they may be subsequently accessed by other medical members or where they may be subsequently accessed for report generation or performance analysis. This data is commonly entered within a single destination such as a hospital information system (HIS).

Such data acquisition and data entry obstacles impose burdens on already constrained resources of the medical care provider and raise costs for already expensive medical care provided by the medical care provider. Additionally, restricting access to the data, managing the data, and efficiently disseminating the data once it is entered within the HIS or other database are issues that further hinder the adoption and raise the costs associated with the use of such central storage solutions within the medical field.

Further complicating the issue are regulations such as the Health Insurance Portability and Accountability Act (HIPAA) that require certain medical data be privileged and thus be prohibited from access by various members of the medical care provider. For instance, while a surgeon of the medical care provider requires access to extensive medical data associated with the health history and treatment of a patient, a billing member of the medical care provider need only view what procedures were provided without having access to detailed information as to how the procedures were rendered or how a patient responded to such procedures.

Information overload is yet an additional concern for the medical care provider. From the above example, the billing member need only access the medical data that is relevant to bill for the services rendered. In some instances, the billing member is provided superfluous data from which the prevalent data must be manually parsed, causing the billing member to lose valuable time and resources. Similarly, information overload hinders those members responsible for treating the patient. Often, the physicians must parse through objective data that is unrelated to the patient's condition or the physicians must determine for themselves which of the data within the notes are relevant. Certain illnesses are best diagnosed or treated by examining only a select set of parameters, however those parameters may be disbursed unevenly and at various locations throughout the notes making it difficult for the physicians to find the relevant data.

Additionally, the data is sometimes unavailable to the parties that require it, because it has yet to be entered into the central database or because there is no efficient means for disseminating the data once it is entered. For instance, the effectiveness of a physician performing rounds is increased when a patient's vitals, labs, and other objective data are available to the physician prior to performing the rounds. Therefore, it would be helpful if such data was available when needed without the manual process of having the physician or the physician's assistant manually pull the data from the database prior to performing the rounds.

Therefore, there is a need to simplify the data aggregation processes used to build and populate the digitized database of medical data for a medical care provider. Of similar importance, is the need to simplify and to reduce the overhead associated with restricting access to the data, managing the data, and disseminating the data once it is entered into the digital database so that efficiency within the medical care provider increases and those members requiring the data are provided the necessary data in a timely manner. Such operations should be automated in an intelligent manner that reduces information overload while still providing relevant data to those members of the medical care provider that need such data.

SUMMARY OF THE INVENTION

Some embodiments provide a system and method for automatedly aggregating medically related data from one or more data sources and disseminating different sets of the aggregated data to two or more different members of a medical care provider. Additionally, some embodiments ensure the completeness of the aggregated data to be disseminated by acquiring subsequent follow-up data when the previously entered data is incomplete. Some such embodiments dynamically generate electronic forms which are sent to the one or more data sources in order to acquire the missing data.

Some embodiments store the aggregated data within a data storage solution. From the storage solution, some embodiments automatedly and intelligently disseminate the aggregated data such that the data that is written once to the data storage solution is usable by a multitude of different members of the medical care provider, each member performing a different set of functions. Some embodiments intelligently disseminate the aggregated data by disseminating only relevant sub-components of the data to different members of the medical care provider. In this manner, some embodiments automatically pre-populate a particular physician's clinical notes with data components related to patients under the care of the particular physician and disseminate the pre-populated notes to a device associated with the physician.

In some embodiments, the data dissemination is based on a set of rules and constraints specified within a dissemination script that determine what sub-components are sent to which members. In some such embodiments, the dissemination is performed by referencing a set of tags associated with the data during aggregation of the data. Some embodiments intelligently disseminate the aggregated data by disseminating only data components of a data record whose values exceed predetermined threshold values. Some embodiments intelligently disseminate the aggregated data by organizing the data so that the most relevant data is provided first.

BRIEF DESCRIPTION OF THE DRAWINGS

The novel features of the invention are set forth in the appended claims. However, for the purpose of explanation, several embodiments of the invention are set forth in the following figures.

DETAILED DESCRIPTION OF THE INVENTION

In the following detailed description of the invention, numerous details, examples, and embodiments of the invention are set forth and described. However, it will be clear and apparent to one skilled in the art that the invention is not limited to the embodiments set forth and that the invention may be practiced without some of the specific details and examples discussed.

I. Overview

Figure 1:
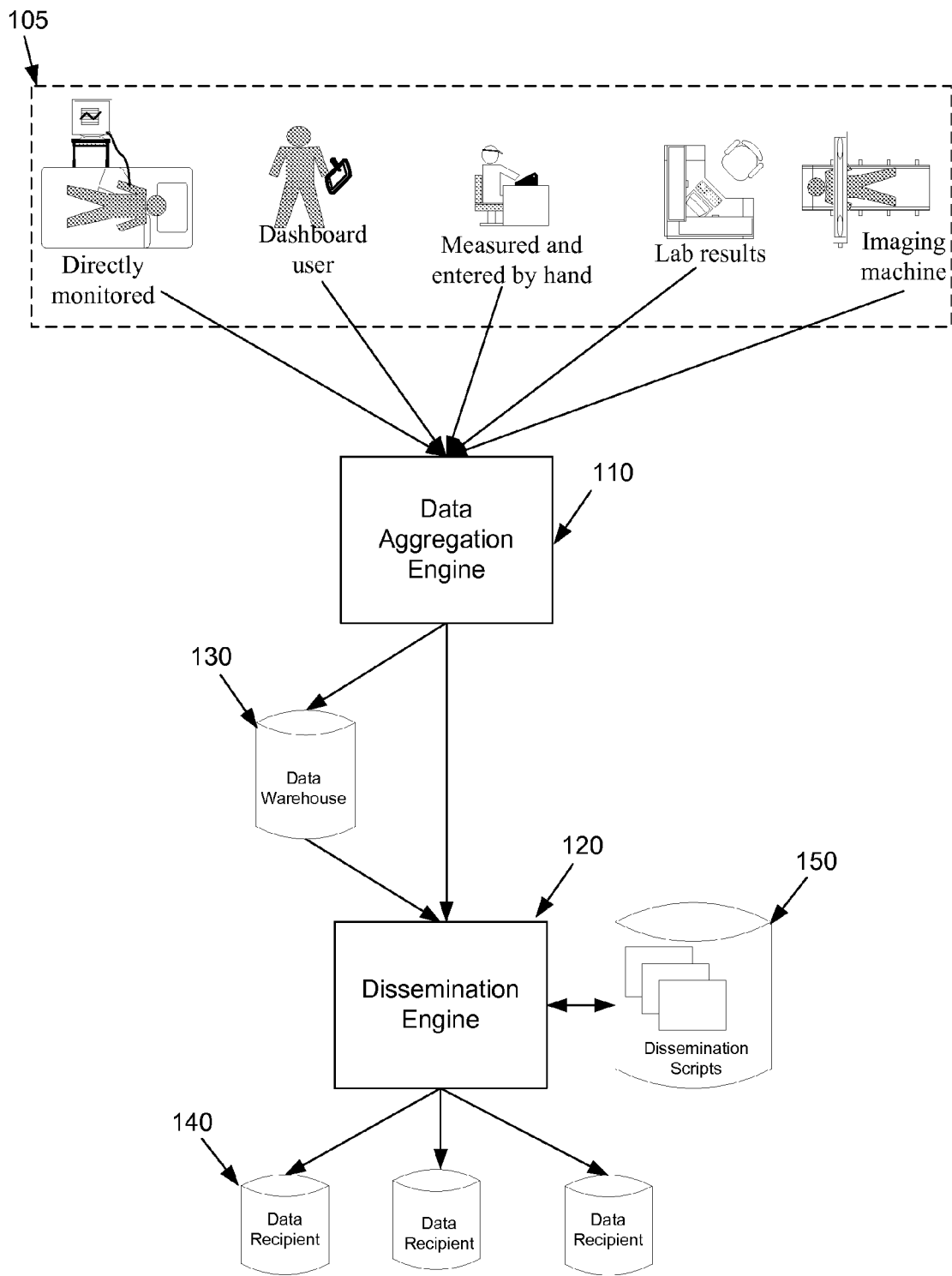
FIG. 1 conceptually illustrates the system of some embodiments of the invention that processes patient data.

FIG. 1 conceptually illustrates system components for an architecture 100 of some embodiments that perform the data aggregation and data dissemination functionality. Such functionality is facilitated by a data aggregation engine 110 that interfaces with a data warehouse 130 and a dissemination engine 120. The dissemination engine 120 disseminates data to one or more data recipients 140 based on one or more dissemination scripts 150.

In some embodiments, the data aggregator 110 receives patient data from one or more disparate patient data sources 105. The data aggregator 110 collects objective data such as vitals from monitors monitoring the patients, lab reports, and medical images (e.g., x-rays, Magnetic Resonance Imaging (MRI), Computed Tomography (CT) scans, etc.) and subjective data such as physicians' assessments, physicians' diagnosis, clinical notes, or physician treatment plans from the various data sources 105.

In some embodiments, the data aggregator 110 collects different data packages (e.g., notes, documents, etc.) of the above described patient data. The data packages include one or more data components containing the objective patient data, subjective patient data, identification information, or other relevant patient information. In some embodiments, the data aggregator 110 forms a patient data record from the one or more collected data packages. The patient data record is a single logical data resource for each patient that includes sets of data components from one or more sources of entered data. The data aggregator then identifies and partitions the sets of data components. Such partitioning allows some embodiments to disseminate different data tuples of the data components to different receiving entities.

Some embodiments generate the data tuples based on data components that are relevant to a receiving entity. In this manner, some embodiments disseminate only the data components of the patient data record that are relevant to the functions of the receiving entity. Each data tuple includes one or more of the data components of the patient data record. Accordingly, a data tuple specifies any subset of data components of the patient data record. As such, each data tuple may include any combination of the data values from the patient record. Additionally, it should be apparent to one of ordinary skill in the art that in some embodiments the data tuples include one or more data components from one or more different patient data records.

To generate the data tuples, the data aggregator 110 of some embodiments tags the collected data to improve subsequent access to and retrieval of the data. In some embodiments, the data aggregator 110 passes the collected data and the associated tags to the dissemination engine 120 for dissemination. In some other embodiments, the data aggregator 110 stores the collected data and the associated tags in the data warehouse 130 for subsequent retrieval by the dissemination engine 120. The data warehouse 130 provides database functionality and operates as a central storage solution for some embodiments.

In some embodiments, the data aggregator 110 and/or dissemination engine 120 process the patient data in real-time. The real-time processing by the data aggregator 110 of some embodiments includes parsing and tagging the collected data as the data aggregator 110 receives new patient data. For instance, the data aggregator 110 regularly pulls data from patient monitoring devices. Alternatively, the data aggregator 110 may operate in an on-demand basis, whereby whenever new data is submitted to the data aggregator 110, the data aggregator 110 performs the parsing and tagging of the data. The real-time processing by the dissemination engine 120 of some embodiments includes generating the various data tuples based on functions performed by each receiving destination immediately after the data aggregator 110 tags the data. The dissemination engine 120 either directly receives the data from the data aggregator 110 in real-time or directly retrieves the data from the data warehouse 130 in real-time. For example, as the data aggregator 110 populates the data warehouse 130, a flag is set whereby the dissemination engine 120 identifies the newly collected data. Additionally, the real-time processing by the dissemination engine 120 includes disseminating the various data tuples to the corresponding destinations once the data tuples are generated.

In some embodiments, the data aggregator 110 and/or dissemination engine 120 perform a batch processing of the patient data. In some embodiments, batch processing by the data aggregator 110 includes collecting, parsing, and tagging the patient data at periodic intervals or upon specified conditions (e.g., when a round of patient monitoring is complete). Similarly, batch processing by the dissemination engine 120 includes generating and disseminating the relevant data tuples to the appropriate destinations at periodic intervals. In some such embodiments, the dissemination engine 120 periodically scans the data warehouse 130 to identify newly collected data that needs to be disseminated.

Furthermore, in some embodiments, one of the data aggregator 110 or the dissemination engine 120 performs real-time processing of the patient data, whereas the other component performs batch processing of the patient data. For example, the data aggregator 110 may periodically collect, parse, and tag patient data as part of a batch process and the dissemination engine 120 processes the collected data in real-time as it is collected at each periodic interval.

Accordingly, the data aggregator 110 and dissemination engine 120 of some embodiments can take a single data package (e.g., a single note, document, etc.) that includes data components produced (e.g., collected and generated) in a single session from a single data collector (e.g., doctor, nurse, administrator, patient monitor, etc.) and disseminate the data components (i.e., data values) of the single data package to one or more destination by breaking its data components into one or more data tuples. In this manner, each destination receives only the data tuples that contain information relevant to the tasks or functions performed by the destination. As noted above, some embodiments perform the processing in real-time as the data aggregator 110 collects the data (referred to below as aggregating data) or as part of a batch process. In conjunction with or instead of processing a single data package at a time, some embodiments (1) aggregate several data packages (e.g., notes or documents) produced in several collection sessions into one aggregated data package (e.g., patient data record) and (2) break the data components of the aggregated data package into multiple different data tuples that are disseminated to multiple different destinations. Such aggregated content may include notes and documents from multiple different data sources, such as subjective data from doctors and nurses, and objective data such as vitals and labs. Additionally, such aggregated content may include notes and documents from one or more sources that were collected (i.e., aggregated) at different instances in time.

Figure 2:
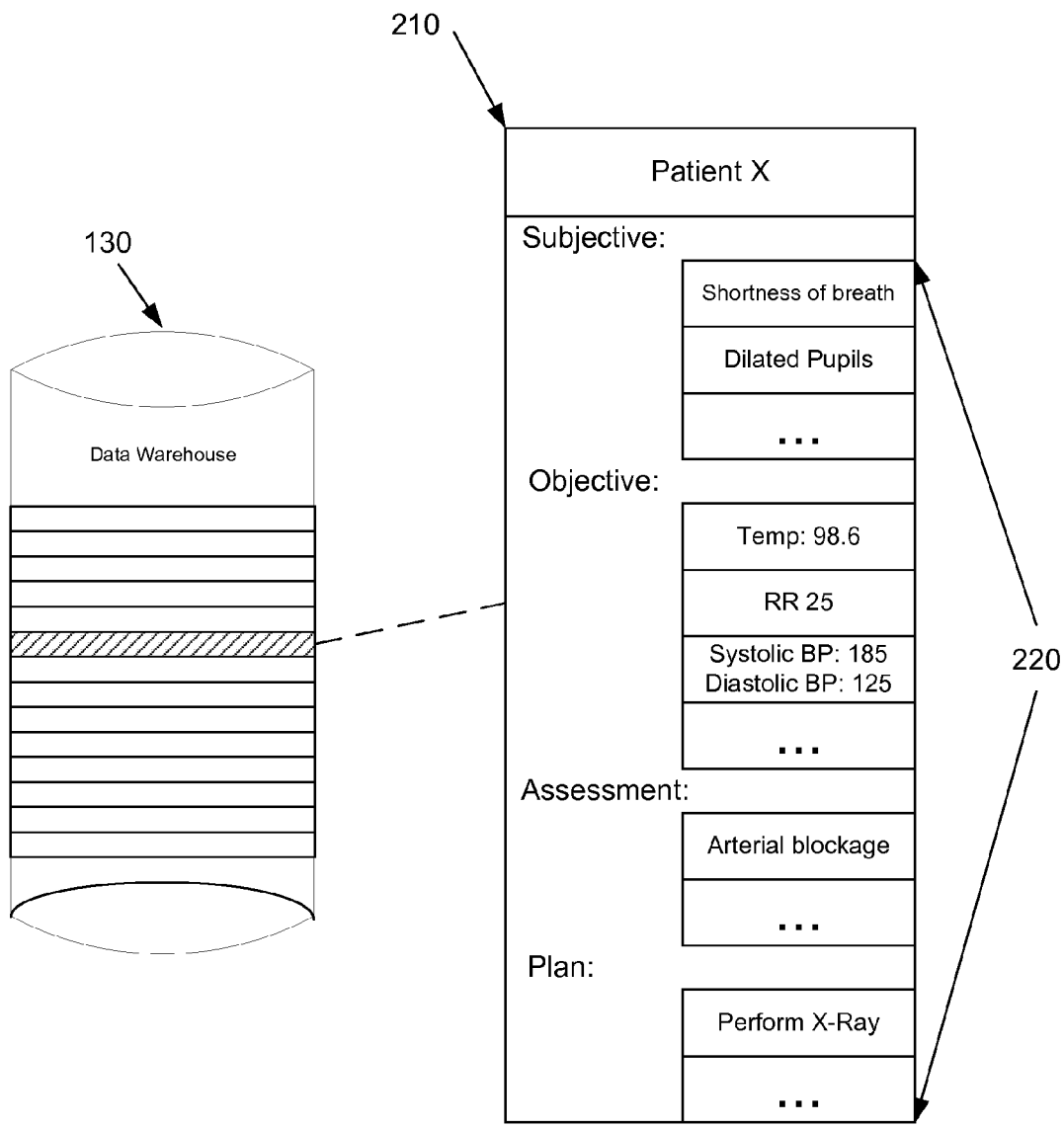
FIG. 2 presents a data record containing data components of a SOAP note in accordance with some embodiments.

In some embodiments, the aggregated data for a patient includes data components of a subjective, objective, assessment, plan (SOAP) note. FIG. 2 presents a data record containing data components of a SOAP note in accordance with some embodiments. The various data components 220 of the data record 210 are automatically populated using the data aggregated by the data aggregator 110. It should be apparent to one of ordinary skill in the art that a data record may include a conceptual data record that is distributed across multiple tables of the data warehouse 130.

Figure 3:
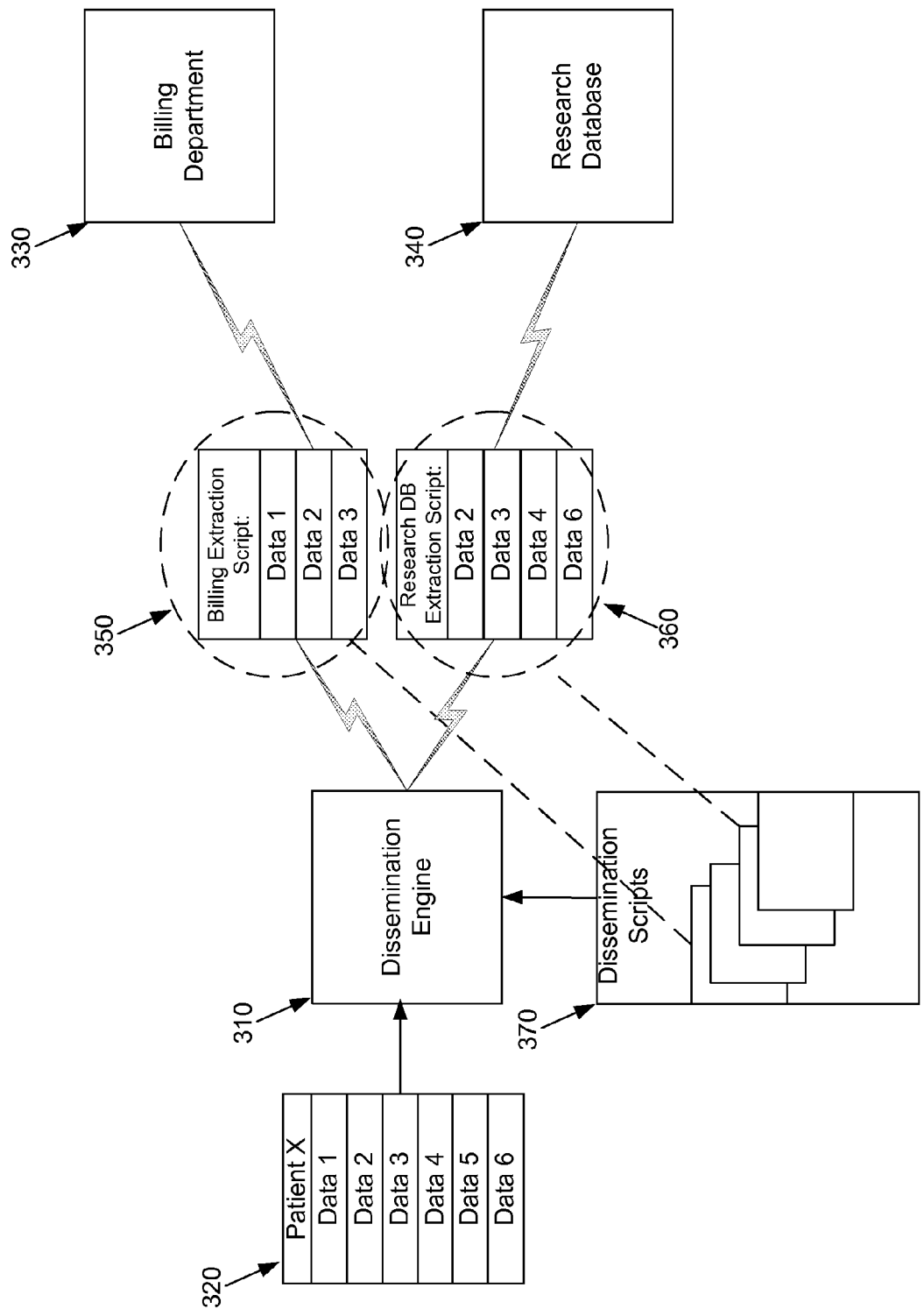
FIG. 3 conceptually illustrates utilizing scripts in accordance with some embodiments in order to control the dissemination of data components of a data record.

FIG. 3 conceptually illustrates the operation of the dissemination engine 120. Specifically, the dissemination engine 120 utilizes one or more dissemination scripts that specify set of rules and constraints for controlling the dissemination of the data components of a data record. In this figure, a dissemination engine 310 retrieves a data record 320. The dissemination engine 310 disseminates some or all of the data record 320 to a billing department 330 of a medical care provider and a research database 340 of the medical care provider. The dissemination is performed based on scripts 350 and 360 that specify the data components of the data record to extract for each corresponding medical care member 330 and 340.

In FIG. 3, the various scripts are stored within a dissemination script database 370. Each script defines the data components rules and policies for disseminating the data components to one or more members. In order to reduce information overload and to reduce the amount of data that is transmitted to the billing department 330, the dissemination engine 310 applies the billing dissemination script 350 to the data record 320. The billing dissemination script 350 specifies the data components that allow the billing department 330 to satisfy their tasks. For instance, the billing department requires only basic data components of a patient's data record such as patient identification information, insurance information, and procedures, labs, and other services performed on the patient. The billing department does not need access to the patient's vitals, physician diagnosis, physician treatment plan, physician assessment, nor the details associated with each procedure, lab, or service performed on the patient. Accordingly, the billing dissemination script 350 specifies that the dissemination engine 310 extract the required data components and omit the unnecessary data when disseminating data to the billing department 330.

The research database 340 requires data related to the patient's illness, but billing related data and patient identification information are unnecessary and should therefore be omitted when the data record is disseminated to the research database 340. Accordingly, the research dissemination script 360 specifies the necessary data components of the data record 320 that the dissemination engine 310 should extract and disseminate to the research database 340 while omitting unrelated information.

It should be apparent to one of ordinary skill in the art that the dissemination engine 310 is a software process that interfaces with the data records stored within the storage solution of some embodiments. Alternatively, the dissemination engine 310 of some embodiments is a separate hardware device that is physically separate from the storage solution and one that also interfaces with the data records stored within the storage solution.

Several more detailed embodiments of the invention are described in the sections below. Section II conceptually describes a detailed system architecture for implementing the data aggregation, tagging, and disseminating functionality in accordance with some embodiments of the invention. Section III describes the automated data aggregation and tagging of some embodiments. Next, Section IV provides a detailed description for the dissemination of the data. Lastly, Section V describes a computer system with which some embodiments of the invention are implemented.

II. System Architecture

Figure 4:
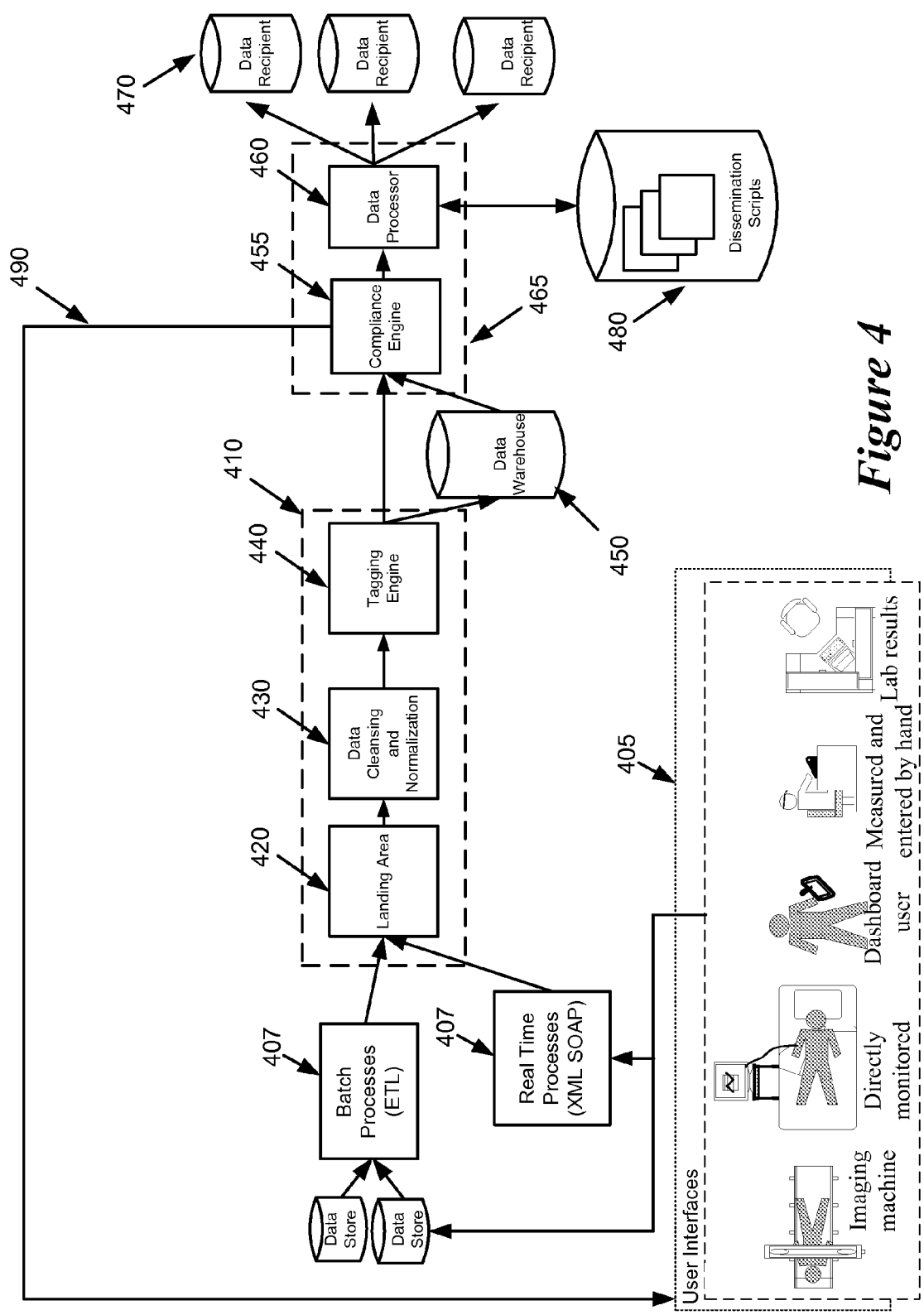
FIG. 4 presents a detailed system architecture in accordance with some embodiments of the invention.

FIG. 4 presents a detailed system architecture in accordance with some embodiments of the invention. Specifically, this figure illustrates the interactions between the various data sources 407 and user interfaces 405 that provide the objective and subjective data for the various sub-components and sub-engines of the data aggregator 410 and dissemination engine 465.

In some embodiments, the user interfaces 405 include a keypad from which data is typed, an auditory transcriber for receiving verbal dictation and transcribing the spoken words in real-time to electronic data, handwriting recognition software, or a drag and drop graphical interface where graphical representations of data can be dragged and dropped into a graphical representation of a SOAP note that is then submitted to the data aggregator. These interfaces are components of different electronic devices such as computers, personal digital assistants (PDAs), smartphones, cellular telephony devices, fax machines, or data sensors linked to monitor health related parameters of a patient. Additionally, other data sources 407 to the data aggregator include different real-time XML Simple Object Access Protocol (SOAP) processing components and Extract-Transform-Load (ETL) batch processing components that may be parts of one or more middleware systems interfacing with the data aggregator 410.

The data aggregator 410 of some embodiments includes a landing area component 420 for receiving the data packages (e.g., user generated notes/documents or sets of data collected by a user or machine) and a data cleansing and normalizing component 430 for uniformly formatting the data components of the data packages. The landing area component 420 permits some embodiments to interface with a variety of different user interfaces 405 and data sources 407 irrespective of the protocols used to transmit the data to the data aggregator 410 by the user interfaces 405 and data sources 407. In some embodiments, data may be pushed into the landing area 420 from physician devices or from patient monitors. Additionally, the landing area 420 of some embodiments directly pulls data from various patient monitoring devices or physician devices to further facilitate the real-time or batch collection of data.

The data cleansing and normalizing component 430 permits some embodiments to interface with a variety of the different user interfaces 405 and data sources 407 irrespective of the data formats that are sent the user interfaces 405 and data sources 407 to the data aggregator 410. When operating in real-time, the data cleansing and normalizing component 430 format the data components of a received data package immediately as the data package is received in the landing area 420. When operating in batch processing mode, the landing area 420 may include a memory buffer from which the data cleansing and normalizing component 430 periodically pull data packages to format. The data aggregator 410 also includes a tagging engine 440 to tag the data with corresponding identification information as it arrives within the data aggregator.

As described above, the dissemination engine 465 receives the aggregated data directly from the data aggregator 410 or from the data warehouse 450. The dissemination engine 465 includes a compliance engine 455 to verify the integrity and completeness of the incoming data and a data processor 460 to disseminate the data to one or more destinations based on a set of policies defined within one or more scripts 480 that work in conjunction with or instead of the data tags.

In some embodiments, the compliance engine 455 verifies whether the data received by the data aggregator 410 is incomplete. Incomplete data may occur when medical care members filling out patient related information using the user interfaces 405 inadvertently omit a particular data component or incorrectly enter a value of the particular data component. Alternatively, incomplete data may occur when data is lost during transmission of the data from the user interfaces 405 to the data aggregator 410. If the data is determined to be incomplete, the compliance engine 455 determines that further follow-up data is necessary. To acquire the follow-up data, the compliance engine 455 either (1) submits a request to one or more particular user interfaces 405 specifying the missing data that is required, (2) modifies data entry forms used by the user interfaces 405 to add, remove, or modify fields within the data interface such that subsequent data submission includes the missing data, and (3) dynamically generates morphing editable forms to send to the one or more user interfaces 405 from which the additional necessary data is to be provided. The feedback loop 490 between the compliance engine 455 and the various user interfaces 405 allows the compliance engine 455 to notify the different user interfaces 405 of the incomplete data. Through the feedback loop 490 and the compliance engine 455, some embodiments ensure the completeness of the data before disseminating the data. As such, the data aggregation process of some embodiments is an iterative process.

Data that is complete can then be processed by the data processor 460 of the dissemination engine 465. The data processor 460 contains the logic for determining which data components of the data records need to be disseminated to which data recipients 470. In some embodiments, these determinations are based on one or more dimensions where a dimension includes disseminating based on the data type, the data value, the data source, the data tag(s), or the data timestamp as some examples. In some embodiments, the data recipients 470 include different members of the medical care provider such as physicians, nurses, billing personnel, quality assurance personnel, quality assurance databases, research databases, etc.

III. Aggregation & Tagging

Some embodiments utilize the data aggregation engine to provide automated data acquisition and data aggregation. The data aggregation engine of some embodiments automatically collects one or more data packages that include medical data associated with a medical care receiving patient from one or more disparate sources within a medical care providing hospital. When collecting multiple data packages, the data aggregation engine also aggregates the data packages into a single aggregated data package. The data packages may include rounding lists that contain patient-specific information for all patients for which a physician or rounding medical team is responsible. Additionally, the data packages may include clinical notes that are generated by physicians periodically on a daily basis or more frequently if needed. Conversely, the rounding lists are generated prior to the time when physicians and residents do scheduled or unscheduled patient rounds. It should be apparent to one of ordinary skill in the art that the collected data packages may include other patient relevant documents or notes that include demographic information, billing information, insurance information, etc.

In many instances, data aggregation is complicated by the fact that the data packages include subjective data entered by medical care members (e.g., physicians, nurses, surgeons, etc.) and objective data received from monitors and imaging devices. In some embodiments, the subjective data includes data related to a patient's admission history, identification information, demographic information, consultation notes, daily progress reports, discharge summaries, operative notes, physician assessments, physician treatment plans, and other clinical documentation. In some embodiments, the objective data includes vitals from bedside monitors, Is and Os, clinical labs, medications, and various imaging such as x-rays and MRIs, etc.

Some embodiments perform the automated data aggregation from the multitude of sources by distributing standardized clinical notes or rounding lists such as subjective, objective, assessment, and plan (SOAP) notes to the data sources. Users or machines then populate the notes. For example, the medical care members write the subjective medical data to an electronic SOAP note that is editable by means of a computer or portable electronic device such as a personal digital assistant (PDA), smartphone, etc. The data aggregation engine collects the populated notes as one or more data packages. If two or more of the collected packages relate to a single patient, the data aggregation engine aggregates all such packages for the patient into a single aggregated package. In some embodiments, the data aggregation engine generates the patient record from the single aggregated package.

It should be apparent to one of ordinary skill in the art that some embodiments use other notes or other data storage items instead of or in conjunction with the SOAP note to collect the aggregated patient data for the data aggregator. For example, the data aggregation engine forms the patient data record from data components of a data package that may be a clinical note, rounding list, billing statement, SOAP note, or other document. Moreover, it should be apparent to one of ordinary skill in the art that the data aggregation engine of some embodiments forms the patient data record from data components of a data package that are collected from a single data source at one or more instances of time or from data components of an aggregated data package that are collected from different data sources at one or more instances of time.

Figure 5:
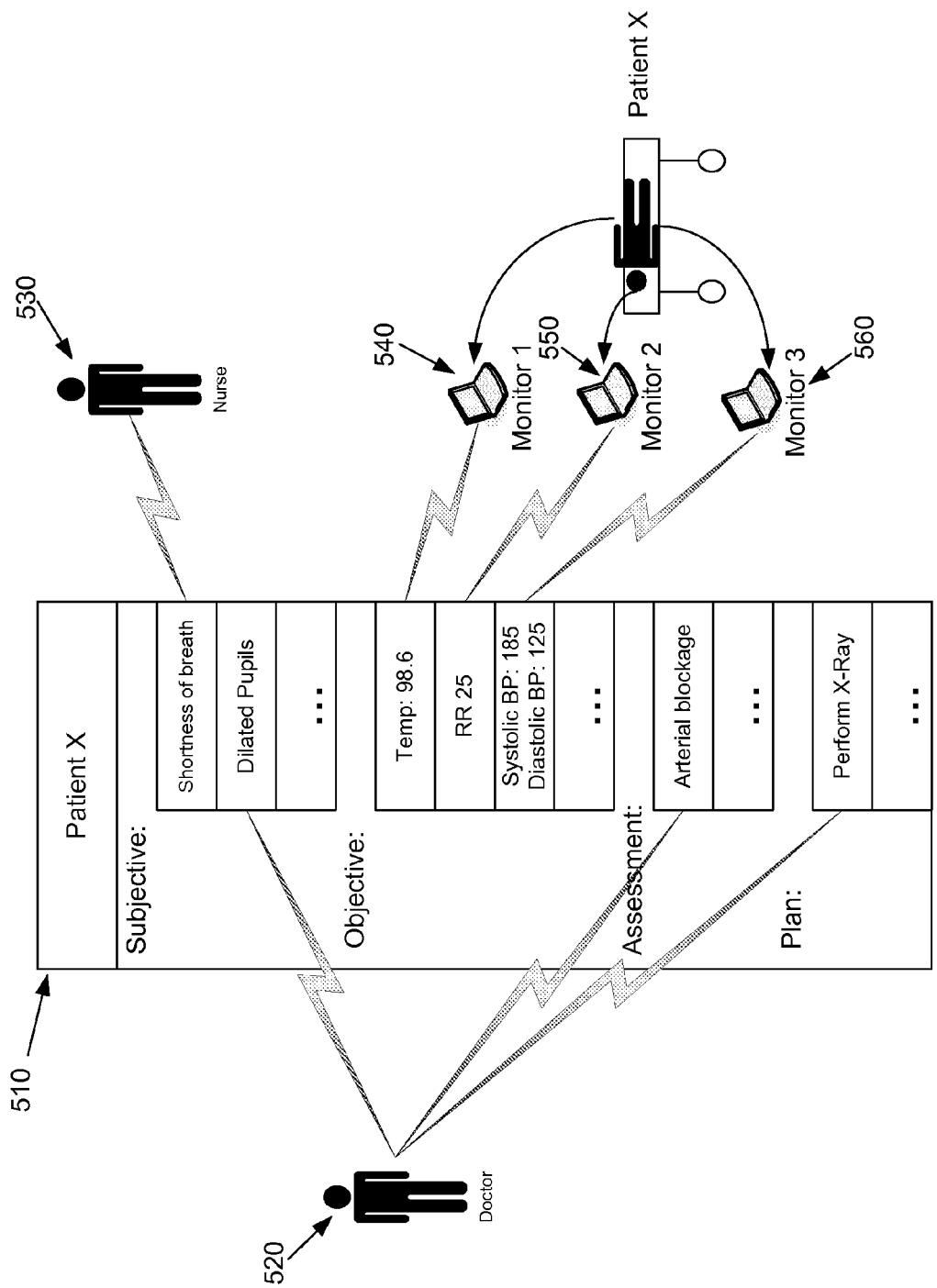
FIG. 5 presents a single shared instance of a SOAP note that is automatically populated with subjective data and objective data.

FIG. 5 presents a single shared instance of a SOAP note 510 that is automatically populated with subjective data and objective data. In some embodiments, the SOAP note 510 represents a data package collected by the data aggregator. As illustrated in the figure, the SOAP note 510 includes multiple data fields that represent the various data components of the data package. Multiple medical care members 520-560 populate the data fields of the SOAP note 510.

As shown, a nurse 530 and physician 520 electronically populate some of the subjective, assessment, and plan fields of the note 510 on an electronic device such as a personal computer or PDA. The data from such devices is automatically pulled by the data aggregator and stored within the single shared note 510. Some embodiments of the digital SOAP note 510 constrain the medical care members 520-560 to providing a predetermined set of data as determined from the format of the SOAP note. To facilitate the subjective data acquisition, some embodiments provide pre-populated drop down lists or check boxes within the SOAP note 510 to acquire the data.

Objective data is pulled from the various monitors 540, 550, and 560 in order to populate the objective data fields of the note 510. The monitors 540, 550, and 560 and other object data acquiring devices are electronically coupled, either wirelessly or through wired network, to the data storage solution (i.e., data warehouse) of some embodiments. Through the wireless or wired link, the data is transmitted from the monitors 540, 550, and 560 and other devices to the storage solution. All such data arrives at a central location where the single instance of the SOAP note 510 is maintained and managed.

In some embodiments, the automatically gathered objective clinical information is made available to users in a uniquely designed workflow optimized format on a variety of computer monitors, tablet and laptop PCs, handheld computers (web-based or thick clients) and even as a paper printouts if necessary. Such information may be automatically aggregated and automatically disseminated to physicians prior to the receipt of the subjective data of the SOAP note in accordance with the dissemination procedures below. Automatically aggregating and disseminating the objective data conserves valuable time for physicians performing rounds as the physicians no longer have to manually collect the data themselves or expend other resources to collect such data.

Such functionality when coupled with editable SOAP notes permits medical care members the ability to examine a patient, enter additional findings, generate a clinical treatment plan, or place medical orders into the note by leveraging the automatically pre-populated data already present within the notes. Additionally, some embodiments organize the aggregated information in a modular fashion in such a way that critical highlights of the patient status are displayed first followed by bullet points for the status of the individual organ systems (e.g. respiratory, cardiac, digestive, neurological, etc.).

Accordingly, it should be apparent to one of ordinary skill in the art that the data from the various sources need not be pulled at the same time, but instead may be pulled at different times. For instance, a nurse following up with a patient may update various charts and diagnosis and a quality assurance member of the medical care provider further updates the subjective data after performing a valuation as to the quality of care after the patient is discharged from the medical care provider.

Additionally, some of the fields such as the objective data fields may be updated in real-time by pulling current data upon the occurrence of different triggering events. For example, the triggering events relate to particular changes in a patient's condition. Specifically, some embodiments pull current data upon detection that the patient is suffering a heart attack, stroke, or when the vitals of the patient pass a specified threshold. In some embodiments, the triggering events relate to scheduled data retrieval of a batch process such that the data is pulled on an hourly or daily basis. In this manner, some embodiments dynamically generate a chronological summary or trend of the objective numerical data (e.g., hemoglobin level in the blood or the body temperature) as it is acquired.

As the fragments of data arrive from the one or more different data sources, the data is stored within a storage solution of some embodiments. The storage solution retains the single instance of the SOAP note for each patient which is shared amongst the medical care members. In this manner, the patient data is centrally stored and updated. Subsequent requests by any member of the medical care provider to access the data will therefore arrive and be processed by the storage solution.

As part of the data aggregation and storage process, some embodiments process the gathered data to provide metadata tags for associating identification information to the data to facilitate subsequent dissemination of the data. To perform the metadata tagging, some embodiments separate the data within the notes into various data components, where each data component includes at least a single data entry or multiple related data entries. Additionally, the separated data components of some embodiments include additional drill-down data sub-components that include or link to further related data entries.

Figure 6:
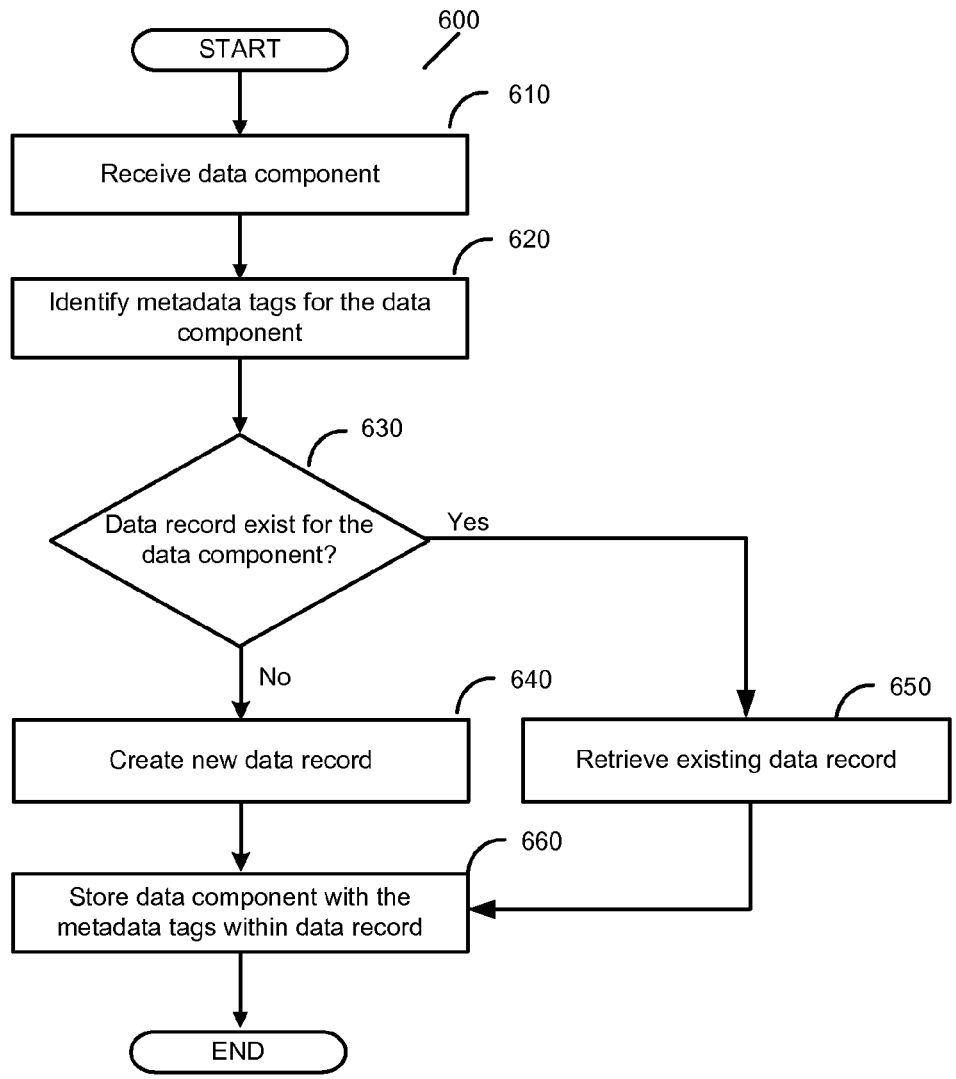
FIG. 6 presents a process for tagging the aggregated data components of an aggregated data record with metadata tags.

FIG. 6 presents a process 600 for tagging the aggregated data components of an aggregated data record with metadata tags. The process 600 begins by receiving (at 610) a data component. The data component may be (1) part of a collected data package, such as a complete SOAP note, that includes many such data components, (2) an update to an already existing data component of a data record such as a periodic update to a vital statistic, or (3) a new data component to an already existing data record such as a new set of x-ray images.

The process identifies (at 620) a set of metadata tags to associate with the received data component. In some embodiments, the metadata provides identification information for the received data component such as source identification, location identification, and temporal identification. Source identification information includes a name or identifier for the medical care member that is the source of the submitted information. The name or identifier relates to personnel within the medical care provider or to various data aggregation monitors (e.g., heart rate, blood pressure, etc.) linked to a patient. The location identification information includes the location from which the data is acquired. Location information generally identifies different wards or departments within the medical care provider (e.g., intensive care unit, emergency room, etc.) or more specifically identifies particular rooms within a ward or department. Temporal identification information specifies a particular timestamp at which the data was received. In this manner, some embodiments retain only the most up-to-date data and are also able to maintain a chronological history of patient data in order to monitor changes in a patient's condition while under the care of the medical care provider. It should be apparent to one of ordinary skill in the art that several additional or different metadata tags may also be associated with the data component.

Figure 7:
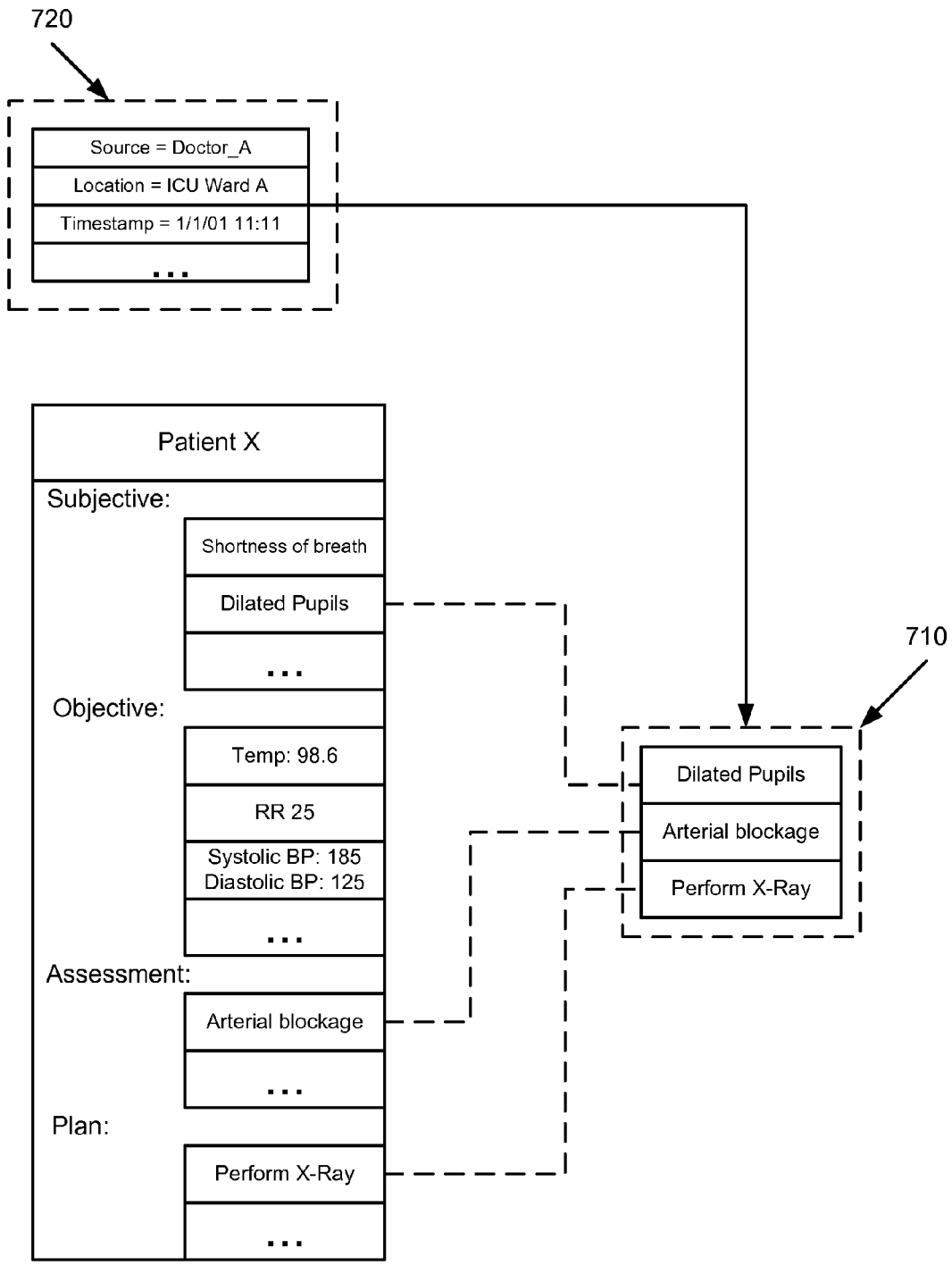
FIG. 7 conceptually illustrates the tagging of the physician entered data of FIG. 5 with source identification, location identification, and temporal identification metadata.

FIG. 7 conceptually illustrates the tagging of the physician entered data of FIG. 5 with source identification, location identification, and temporal identification metadata. As illustrated, the data components 710 entered by the same source at the same time receive the same metadata 720. The data components 710 are separated from the rest of the data record in order to identify and associate proper metadata to the remaining data components which may have arrived from different data sources or at different times.

In some embodiments, the process identifies (at 620) metadata tags that restrict access to received data. In this manner, some embodiments are able to manage access rights to a data component by different medical care members of the medical care provider. These metadata tags identify who or what has permission to access the particular data component. In some embodiments, the various medical care members that may access data include different personnel within the employment of the medical care provider (e.g., physicians, nurses, surgeons, administrative staff, billing personnel, etc.), associates working in conjunction with the medical care provider (e.g., health insurance companies), different departments of the medical care provider (e.g., intensive care unit, nursing, emergency room, post-operative care, billing, etc.), and different databases that utilize the data to generate various reports (e.g., performance or qualitative) or for research purposes. Such access control tags are determined from the data component source.

After the relevant metadata tags are identified (at 620), the process attempts (at 630) to retrieve the data record for the data component. If the received data relates to a previously admitted patient, then the data record exists and an already existing field within the data record needs to be updated or a new field needs to be created. The process retrieves (at 650) the existing record for updating. However, if the received data relates to a newly admitted patient for which a data record does not exist, then the process must create (at 640) a new data record for the patient. The received data and the associated metadata tags can then be stored (at 660) within the data record where the data is accessible by various different members of the medical care provider.

IV. Dissemination

Some embodiments intelligently disseminate the various data components of the one or more collected data packages to one or more destinations according to various dissemination scripts. The dissemination scripts contain the heuristics, rules, and other decision making constructs controlling the manner in which the data is disseminated. In some embodiments, the dissemination decisions are based on several dimensions which may include the metadata tags provided above. In some embodiments, the data dissemination occurs in real-time as the data aggregator collects the data packages and optionally aggregates the data packages. In other embodiments, the data dissemination occurs as a batch process scheduled to run at various periodic intervals or as instantiated by a system administrator.

Figure 8:
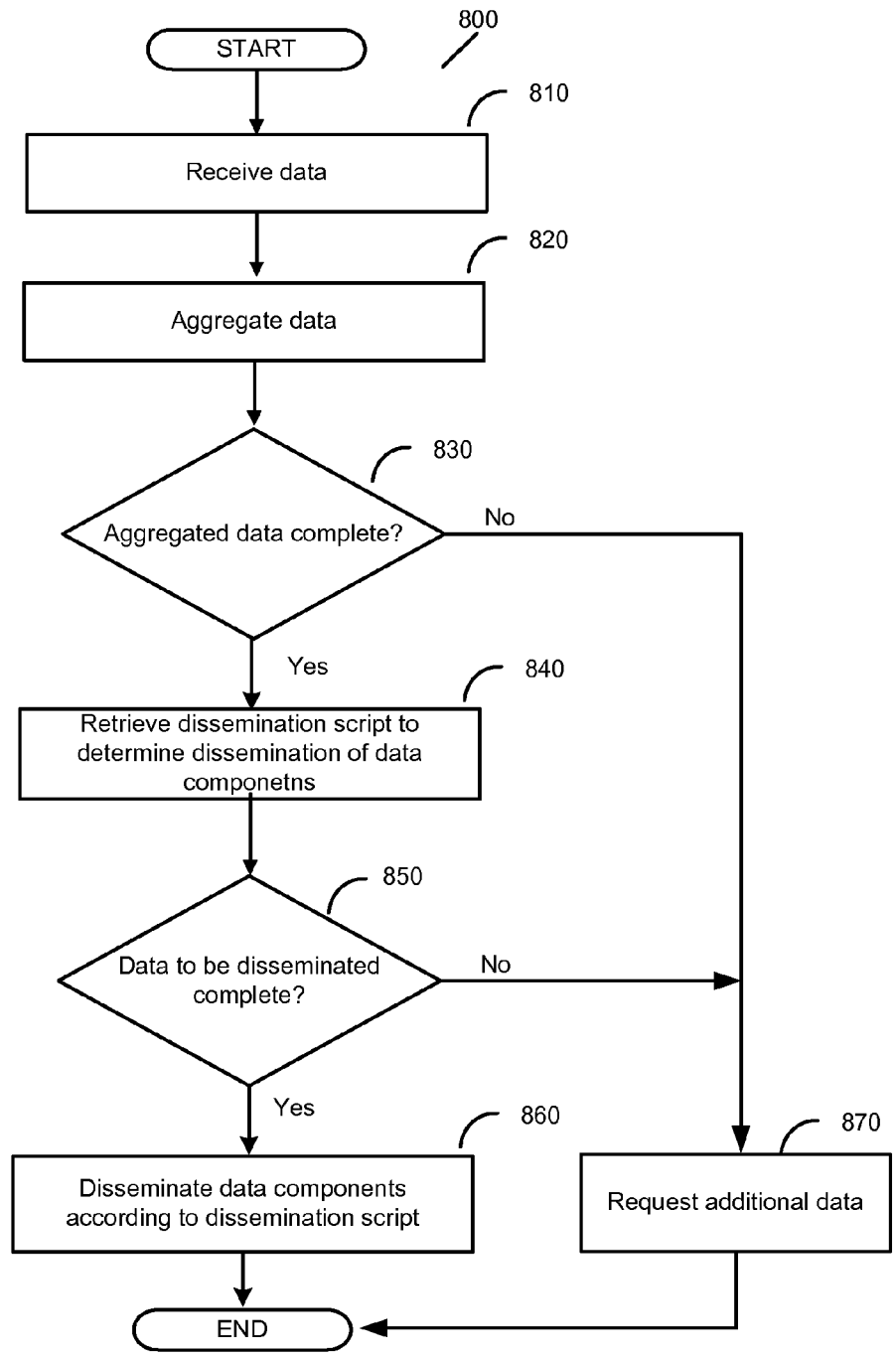
FIG. 8 presents a process for ensuring data completeness in accordance with some embodiments of the invention.

As noted in the system architecture of FIG. 4, some embodiments of the dissemination engine first perform one or more data compliance checks to ensure completeness of the data to be disseminated. FIG. 8 presents a process 800 for ensuring data completeness in accordance with some embodiments of the invention. The process 800 begins by receiving (at 810) data from one or more data sources through the data aggregator. As mentioned above, the data aggregator will aggregate (at 820) the data when receiving data for a single patient from multiple sources. The collected data undergoes (at 830) a first series of compliance checks that determine whether the collected data is complete. This first set of compliance checks verifies whether all transmitted data from the various data sources is received by the data aggregator. Packet loss over the network may result in incomplete aggregated data. Additionally, some embodiments verify that a particular set of data components from one or more objective data monitors are reported at specified intervals. When data from a monitor is not received during a particular interval then the process deems the data incomplete.

When the collected set of data is determined to be incomplete, the process submits a request (at 870) to a data source to provide the missing data. Otherwise, the process proceeds to retrieve (at 840) a dissemination script. The dissemination script determines the data components of a single or aggregated data package to be extracted and grouped into one or more data tuples for dissemination to one or more destinations. After retrieval of the dissemination script, the process then verifies (at 850) the completeness of the data with respect to the dissemination script using a second set of compliance checks.

In some embodiments, the dissemination script specifies various data components that must be present before disseminating the data. For instance, an admitted patient may have under undergone a battery of tests for a particular ailment, however the second set of compliance checks determines that a particular test was omitted as part of standard procedural treatment for the particular ailment. In other embodiments, the dissemination script requires that data components from multiple data sources (e.g., multiple data monitor) be present prior to dissemination. In still other embodiments, the dissemination script may require particular values for the data components prior to dissemination. It is sometimes the case that medical care members filling out patient related information inadvertently omit a particular data component or incorrectly enter a value of the particular data component and thus the data to be disseminated is incomplete.

If the process determines (at 850) that the data to be disseminated is incomplete, the process submits a request (at 870) to a data source to provide a data package with the missing data components. If the data is complete, the process disseminates (at 860) data tuples per the policies defined within the dissemination script. It should be apparent to one of ordinary skill in the art that some embodiments perform only a single set of compliance checks between the data aggregation and data dissemination operations of some embodiments while other embodiments include additional compliance checks at various different stages of the operations. Additionally, it should be apparent to one of ordinary skill in the art that in some embodiments the compliance checks are optional and thus are not always performed. Some embodiments disseminate the acquired data, as will be described in further detail below, as the data is received, parsed, and tagged by the data aggregator without performing the completeness checking described with reference to FIG. 8.

Figure 9:
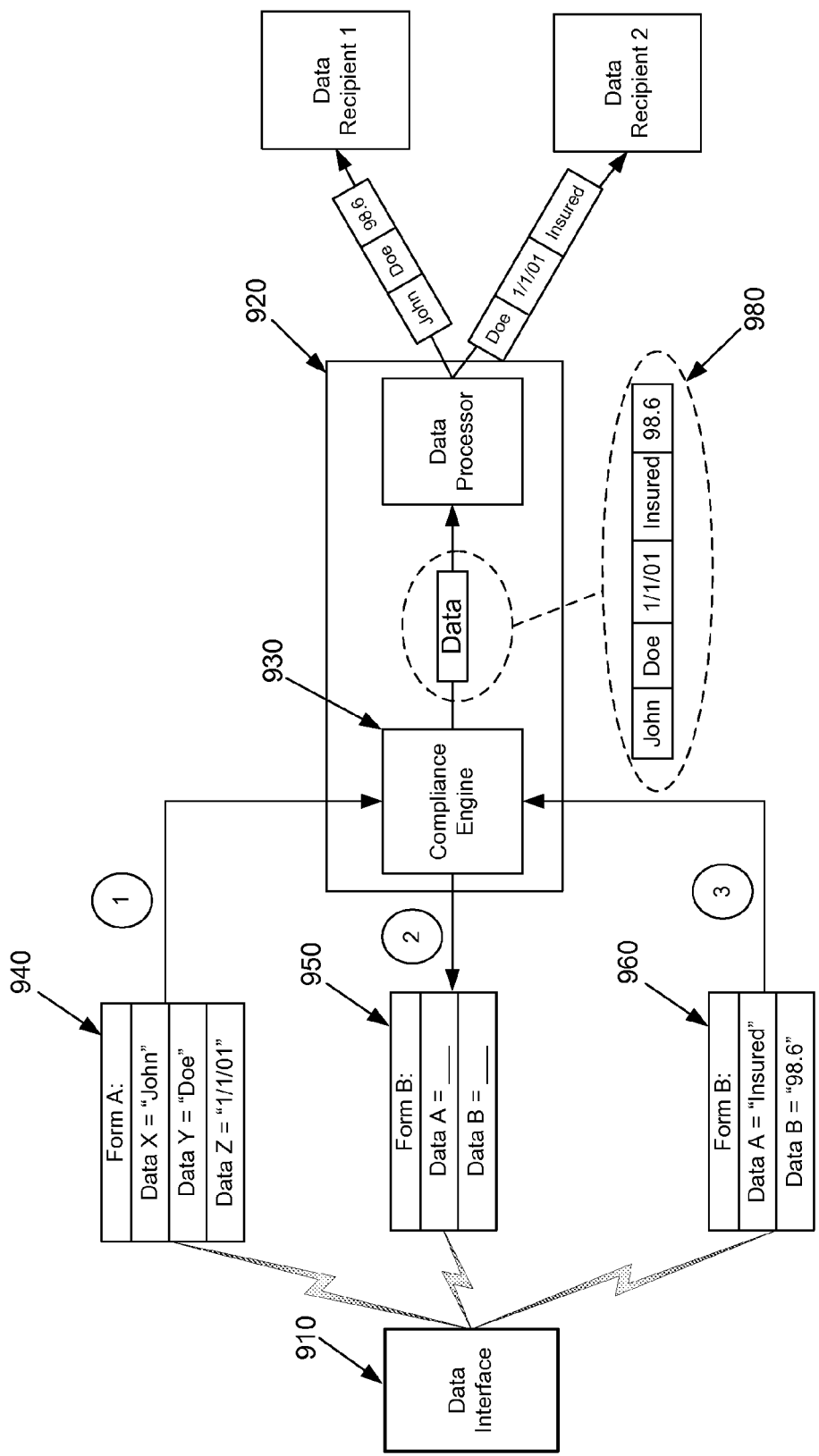
FIG. 9 illustrates the acquisition of missing data using dynamically generated editable forms in accordance with some embodiments.

FIG. 9 illustrates the acquisition of missing data using dynamically generated editable forms in accordance with some embodiments. In this figure, a first predetermined editable form 940 is completed and submitted by the data interface 910 to enter an initial set of data. It should be apparent to one of ordinary skill in the art that some embodiments utilize a set of predetermined editable forms for initial data entry, where different editable forms are sent based on a classification or purpose of the data entrant.

Based on the values within the various data components of the editable form 940, some embodiments of the compliance engine 930 analyze the data to determine that further follow-up information is needed in order to fully satisfy the data requirements for an associated data record. A follow-up form 950 is disseminated from the compliance engine 930 to the data interface 910 requiring a set of follow-up data components to be populated by the data interface 910. From the data interface 910, a completed follow-up form 960 is received with the data field populated providing the missing data. With the data record 980 now complete, the data processor of the dissemination engine 920 may disseminate various data tuples to one or more data recipients where the data tuples includes different combinations or subsets of the data components of the completed data record 980.

In some embodiments, the follow-up form 950 is dynamically generated by the compliance engine 930 based on the particular data determined to be missing or incomplete. Moreover, in some embodiments, the follow-up form 950 is disseminated even when the data components of the initial form 940 are complete in order to request subsequent data that is more detailed or subsequent data that iteratively follows from the initial entered data set. This form of iterative drill-down data compliance checking performed by some embodiments is useful for example when a surgeon submits through the data interface 910 a surgical request specifying a type of surgery required by a patient. The compliance engine 930 analyzes the data and sends a subsequent form to the data interface 910 requesting additional more detailed information regarding the particular type of surgery to be performed and the resources needed to perform the operation. In this manner, the editable forms morph based on the subsequent data to be acquired.

It should also be apparent to one of ordinary skill in the art that in some embodiments, the follow-up form 950 is only a notification of the missing data components illustrated in 950. In such embodiments, it is up to the data interface 910 to manipulate the data entry display to acquire the missing data components or automatically retrieve the missing data from a data store.

Once the data passes the various compliance checks, some embodiments of the invention intelligently and automatedly disseminate individual components of the data record to relevant destinations within the medical care provider. In some embodiments, these components are grouped into data tuples. The data tuples include a subset of data components or data values of the data record that are relevant for the functions or tasks performed by entity receiving the data tuple. In this manner, data that is written once to a central storage solution is subsequently disseminated to multiple different destinations for multiple different uses. Such different uses include disseminating some or all of the data to facilitate billing, research, quality assurance, and medical record sharing amongst different units as some examples. Some embodiments disseminate the pieces of data via e-mail, fax, SMS, paging system of the medical care provider. Each manner of dissemination may include different protocols and wired or wireless means for disseminating the data.

To perform the data dissemination, some embodiments utilize scripts that determine the one or more destinations for each data tuple in conjunction with or instead of the metadata specified during data storage. The scripts include one or more dimensions that formulate the rules and constraints determining dissemination policies. Scripts may be written per policies defined by a system administrator of the central storage solution, a member of the data recipient, or from a collaboration between both.

In some embodiments, the dimensions of the script define the data components of the data record to extract into the various data tuples, the frequency for data dissemination, the one or more destinations to send the extracted data to, and any additional processing that is to occur to the extracted data tuples prior to dissemination. In some embodiments, the dimensions perform the desired dissemination operations by analyzing the metadata tags associated with the data such as the source of the data, the type of the data, the timestamp for when the data was received, etc. By using the dissemination script to restrict which members are able to access what data, some embodiments minimize the amount of data exchanged between various members of the medical care provider and reduce information overload while maintaining security policies and access rights.

Figure 10:
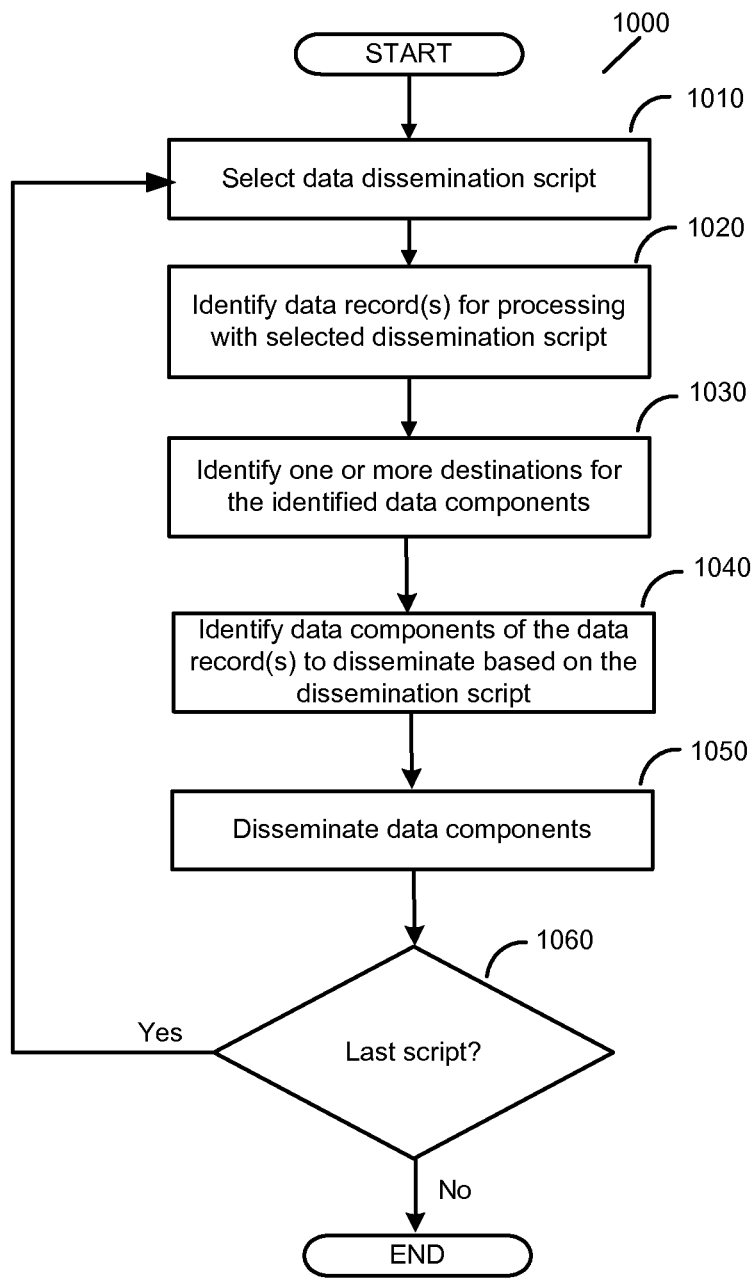
FIG. 10 presents a process for disseminating data to one or more data recipients based on a dissemination script in accordance with some embodiments.

FIG. 10 presents a process 1000 for disseminating data to one or more data recipients based on a dissemination script in accordance with some embodiments. The process 1000 begins by selecting (at 1010) a data dissemination script to process. The process identifies (at 1020) one or more data records for processing with the dissemination script. The process then identifies (at 1030) the one or more destinations for receiving the identified data. The destinations include one or more members of the medical care provider, such as clinical staff (e.g., physicians and nurses), clerical staff (e.g., administrators and billing personnel), data monitors, research databases, quality assurance databases, and other electronic interfaces of the medical care provider.

Figure 11:
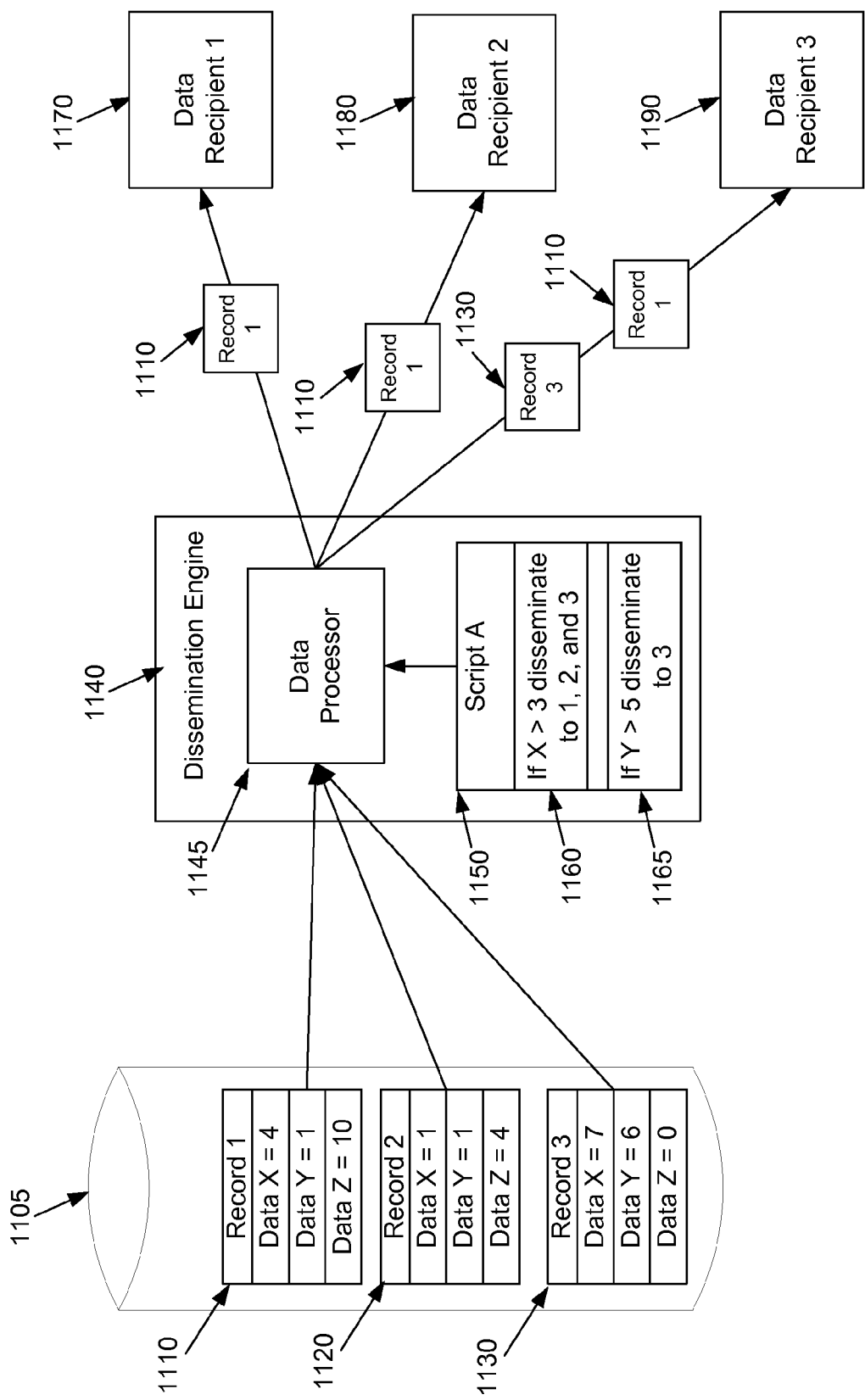
FIG. 11 illustrates the processing of the values of the data components prior to data dissemination.

From the identified destinations, the process identifies (at 1040) the various data components of the data record(s) for the data tuple(s) to disseminate based on the various dimensions and policies of the dissemination script. Since different destinations may receive different data tuples with different subsets or combinations of the data components, the identification of the data components may differ per destination. Moreover, some embodiments perform further processing of the data components prior to dissemination of the data. FIG. 11 below illustrates the processing of the values of the data components prior to data dissemination and FIG. 12 below illustrates the automated organization of data prior to data dissemination.

After analysis of the data record is complete and the destinations are identified, the process electronically disseminates (at 1050) the identified data tuples to the one or more proper destinations. The process then examines (at 1060) whether any remaining dissemination scripts remain for processing. If no other scripts remain, the process terminates. Otherwise, the process reverts back to step 1010 and selects the next script to process.

It should be apparent to one of ordinary skill in the art that in some embodiments the process 1000 of FIG. 10 executes in real time as data records are collected by the data aggregator. Alternatively, the process 1000 of FIG. 10 may execute as a batch process at specific periodic intervals or as instantiated by a system administrator. Moreover, some of the scripts are destination specific and therefore for each destination a script is processed whereas in other instances, the scripts process data records for multiple destinations.

Some embodiments utilize the data dissemination process 1000 of FIG. 10 in order to automatically pre-populate clinical notes and patient rounding lists for hospitalized patients. The notes can be generated for physicians periodically on a daily basis or more frequently if needed. The rounding lists are generated prior to the time when physicians and residents do scheduled or unscheduled patient rounds and the disseminated data within the lists contain patient-specific information for all patients for which the physician or rounding medical team is responsible. Moreover, these notes are made editable so that after the physician or the medical team examines the patient they can enter their findings to be subsequently aggregated with pre-populated data. The data can then be further disseminated to various other destinations in an iterative manner.

As mentioned in FIG. 10, some embodiments perform intelligent data dissemination based on conditions specified within the dissemination scripts. Some such scripts contain heuristics that analyze the values of the various data components. FIG. 11 illustrates an example of intelligent data dissemination by processing values of the data components in order to determine whether to disseminate the data component in accordance with some embodiments.

The figure includes a data warehouse 1105 that stores data records 1110, 1120, and 1130. The data records 1110, 1120, and 1130 are processed by the dissemination engine 1140 according to the dissemination script 1150. The dissemination script 1150 contains various conditions 1160 and 1165 that the values of the data components for the data records 1110, 1120, and 1130 must satisfy in order to be disseminated as one or more data tuples to one or more data recipients 1170, 1180, and 1190.

Specifically, a first condition 1160 of the dissemination script 1150 specifies disseminating the entire contents of a data record only when the value for a data component X is greater than a value of 3. Additionally, the condition 1160 specifies that all data recipients 1170, 1180, and 1190 are to receive the entire contents of the data record when the value for data component X exceeds a value of 3. As a result, when the data processor 1145 of the dissemination engine 1140 retrieves and processes the data records 1110, 1120, and 1130, the data processor 1145 determines that only records 1110 and 1130 satisfy the condition 1160 and therefore only records 1110 and 1130 are disseminated to the data recipients 1170, 1180, and 1190.

Similarly, a second condition 1165 of the dissemination script 1150 specifies disseminating the entire contents of a data record only when the value for a data component Y is greater than a value of 5. Additionally, the condition 1165 specifies that only data recipients 1190 receive the data record when the value for data component Y exceeds a value of 5. As a result, when the data processor 1145 retrieves and processes the data records 1110, 1120, and 1130, the data processor 1145 determines that only record 1130 satisfies the condition 1165 and therefore only record 1130 is disseminated to the data recipient 1190.

The threshold value processing illustrated in FIG. 11 reduces information overload by disseminating data components of a data record only upon specified triggering events. The specified triggering events may relate to the occurrence of predetermined significant events, such as when heart rate values within a data component of the data record suggest that a patient is experiencing a heart attack or when respiratory rates within a data component of the data record suggest that the patient is experiencing cardiac arrest.

In this manner, some embodiments provide dynamic data dissemination such that a physician on call may be notified via email or a page that a patient under his care is experiencing complications and the email or page may include the values from the data component to detail the perceived complication. Valuable time is saved and the quality of care is improved as physicians may respond quicker than in prior art solutions where a monitor attached to a patient would notify nearby medical care personnel who would then check the condition of the patient before relaying the complication to the physician on call.

As part of the data dissemination process, some embodiments intelligently process the data to be disseminated by organizing the data so that the most pertinent information is displayed first and ancillary data is displayed last or is omitted. Such intelligent data processing reduces the information overload that could otherwise occur when disseminating to a data recipient all the data that the data recipient is otherwise privileged to view.

Figure 12:
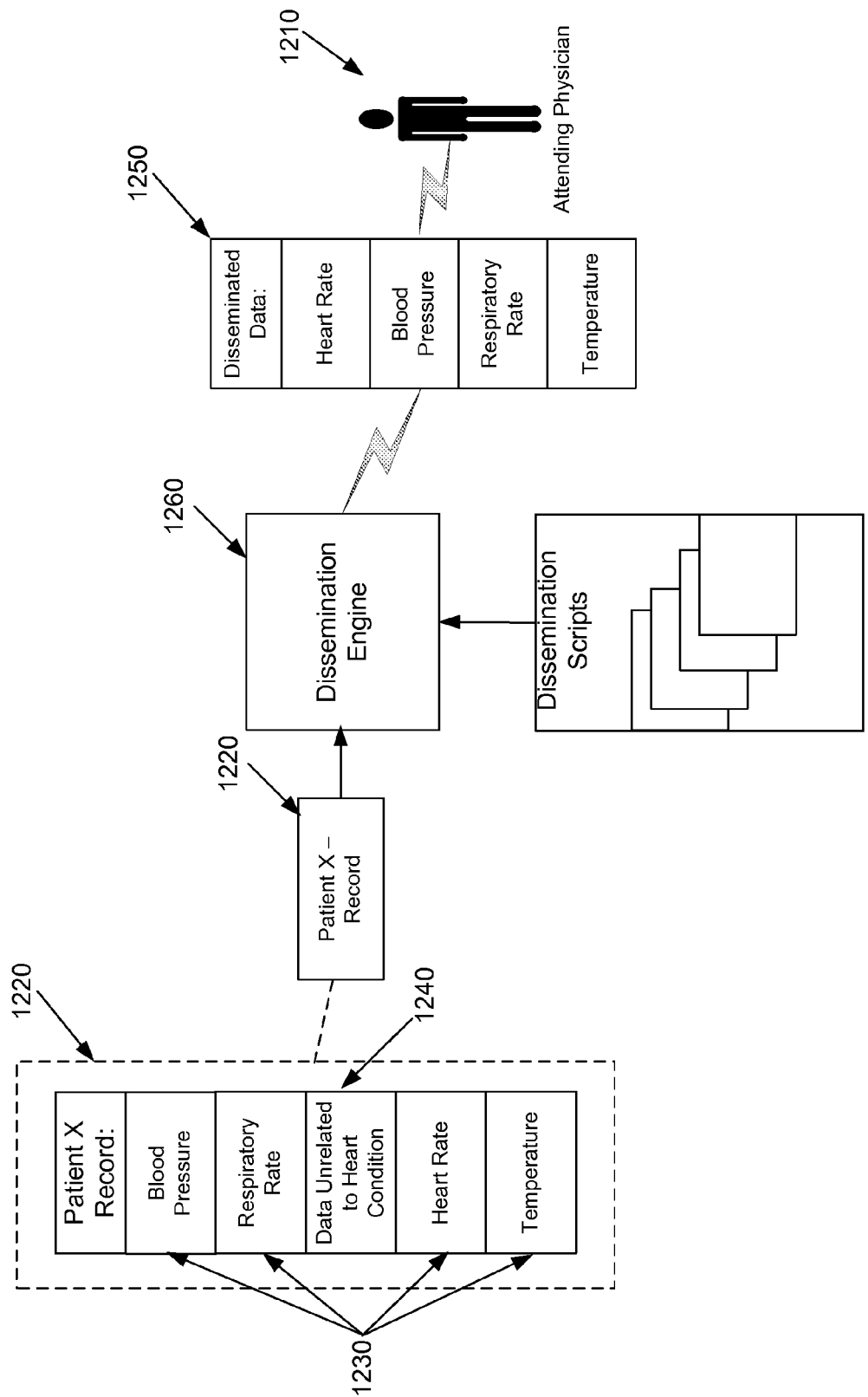
FIG. 12 illustrates the automated organization of data prior to data dissemination.

FIG. 12 conceptually illustrates the organizing of accessible data based on parameters determined to be most relevant to a physician providing care to a patient in accordance with some embodiments. In this figure, an attending physician 1210 is to be provided the data record 1220 for a patient who has a heart condition and who is under the care of the attending physician 1210. The data record 1220 is populated with a set of data components related to the patient's heart condition 1230. Specifically, the heart condition related data components 1230 include blood pressure statistics, heart rate statistics, and temperature statistics. Additionally, the data record 1220 contains a set of data components that are unrelated to the patient's heart condition 1240.

During data dissemination, some embodiments of dissemination engine 1260 analyze the data components within the data record 1220 to determine that the patient is being treated for the heart condition and the physician 1210 is a member responsible for providing the treatment for the heart condition. As such, some embodiments organize the data components 1230 and 1240 of the data record 1220 into a data tuple where the set of data components related to the patient's heart condition 1230 are provided to the physician and the data components unrelated to the heart condition 1240 are omitted.

Moreover, some embodiments associate different weights to each data component such that a first data component related to the heart condition (i.e., heart rate) is deemed more pertinent than a second data component related to the heart condition (i.e., temperature). Based on the determined weights, the individual data components related to the heart conditions are organized within the data tuple in a manner where the data component that is most pertinent to the patient's condition is presented first in the disseminated data tuple 1250.

In FIG. 12, the data unrelated to the heart condition is not transmitted to the data recipient. However, it should be apparent to one of ordinary skill in the art that such information may be disseminated along with the data related to the heart condition albeit in a less emphasized manner, such as a separate data sheet, smaller font, or simply being presented at the end of the disseminated data tuple 1250.

Figure 13:
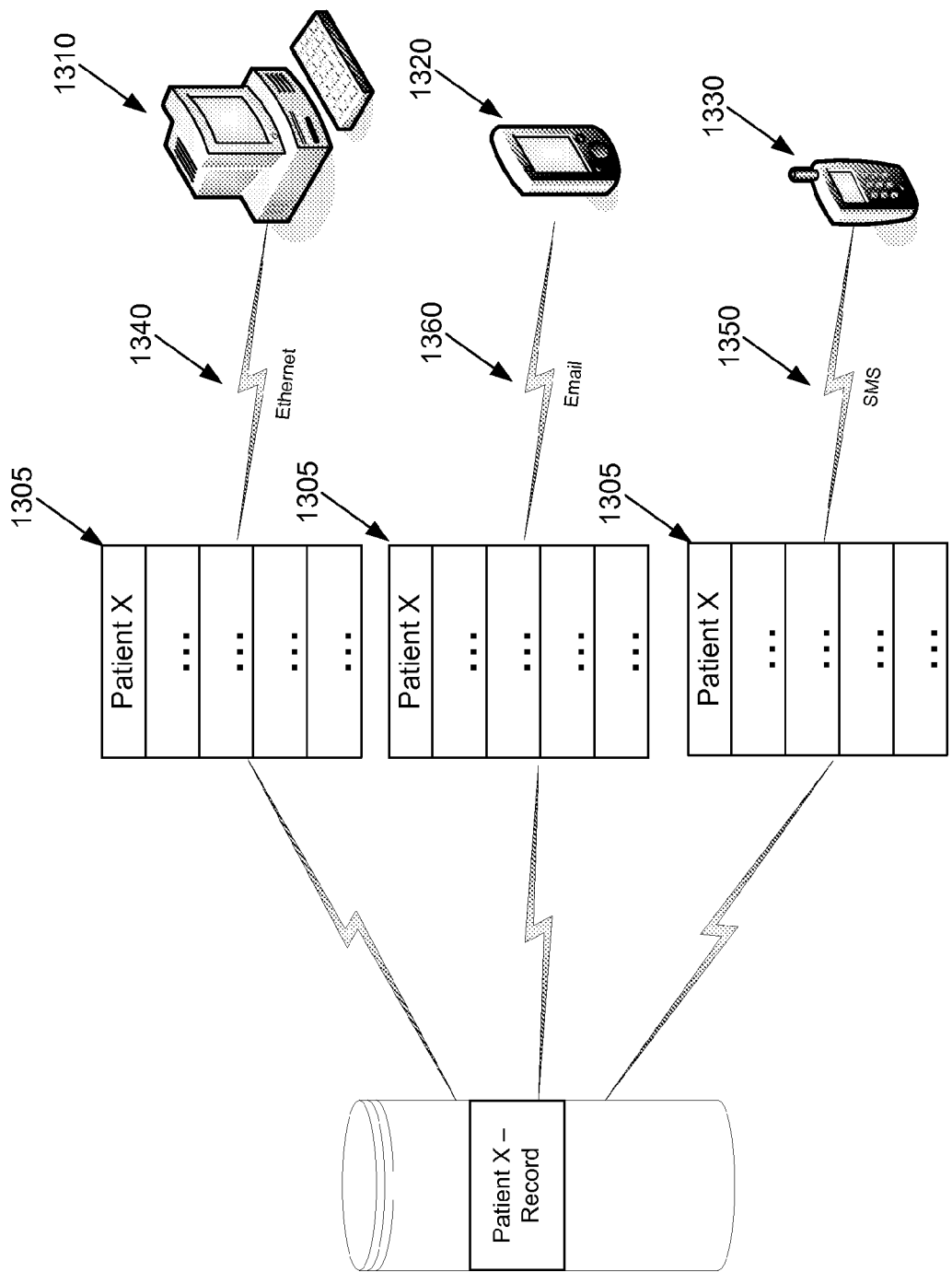
FIG. 13 illustrates the disseminating of data to computer systems, portable digital assistants, and smartphones as some examples.

Some embodiments disseminate the data tuples through a variety of electronic means to a variety of devices. As illustrated in FIG. 13, some embodiments disseminate the data tuples 1305 to computer systems 1310, portable digital assistants 1320, and smartphones 1330 as some examples. The means for transmission between each of the various devices may vary. Some embodiments utilize wired data transmission such as LAN based Ethernet 1340, whereas other wireless means of communication, such as Short Message Services (SMS) 1350 may alternatively be used. Moreover, different protocols for data dissemination are also possible. As shown in FIG. 13, in addition to Internet Protocol (IP) based messaging 1340 and SMS messaging 1350, some embodiments utilize email 1360 to disseminate the data 1305. Once disseminated to the device, the data 1305 is made available for display on a screen of the device.

V. Computer System

Figure 14:
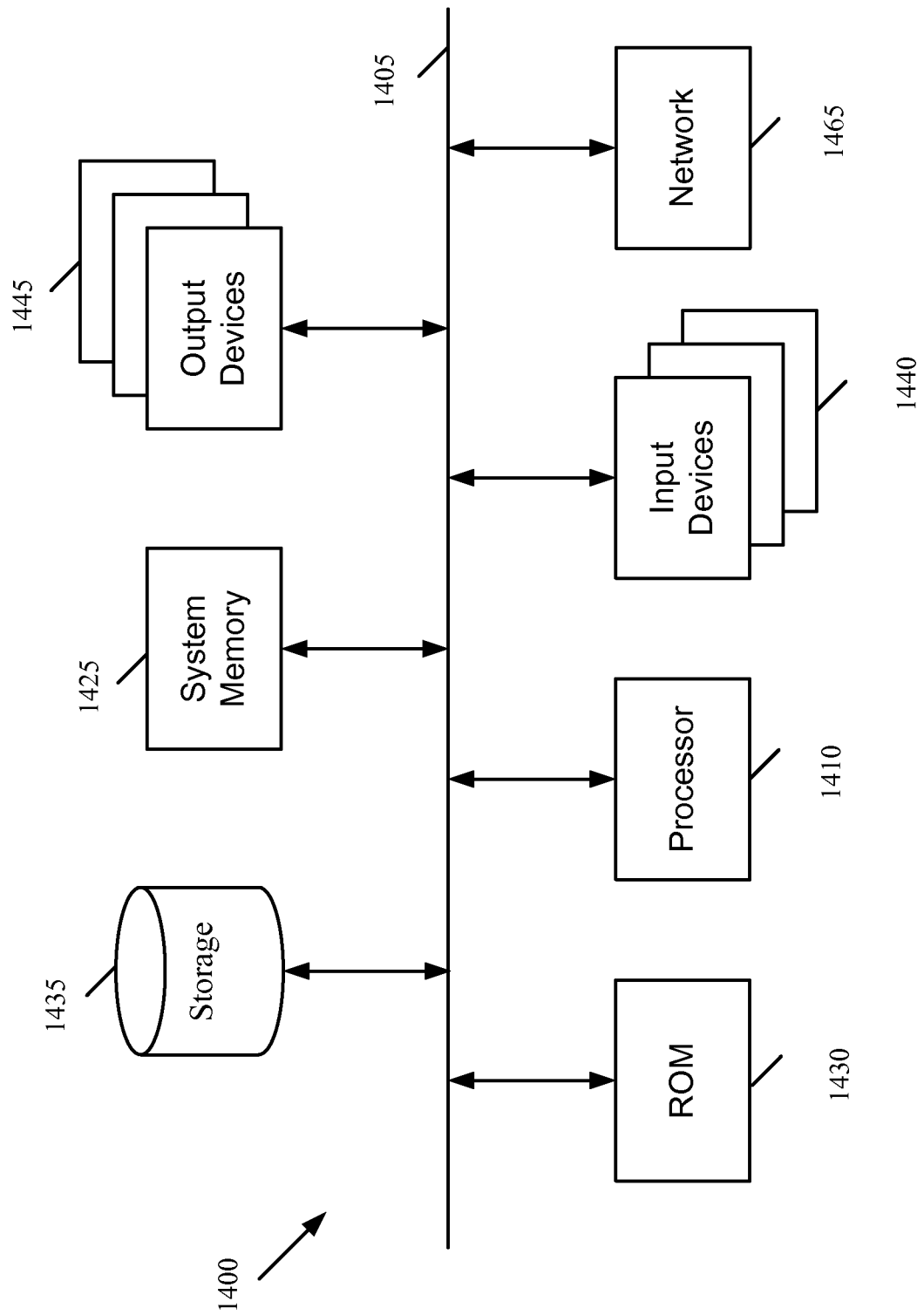
FIG. 14 illustrates a computer system with which some embodiments of the invention are implemented.

FIG. 14 illustrates a computer system with which some embodiments of the invention are implemented. Computer system 1400 includes a bus 1405, a processor 1410, a system memory 1425, a read-only memory 1430, a permanent storage device 1435, input devices 1440, and output devices 1445.

The bus 1405 collectively represents all system, peripheral, and chipset buses that communicatively connect the numerous internal devices of the computer system 1400. For instance, the bus 1405 communicatively connects the processor 1410 with the read-only memory 1430, the system memory 1425, and the permanent storage device 1435.

The various memory units 1425, 1430, and 1435 are parts of the computer system's 1400 computer readable medium from which the processor 1410 retrieves instructions to execute and data to process in order to execute the processes of the invention. The read-only-memory (ROM) 1430 stores static data and instructions that are needed by the processor 1410 and other modules of the computer system. The permanent storage device 1435, on the other hand, is a read-and-write memory device. This device is a non-volatile memory unit that stores instructions and data even when the computer system 1400 is off. Some embodiments of the invention use a mass-storage device (such as a magnetic or optical disk and its corresponding disk drive) as the permanent storage device 1435.

Other embodiments use a removable storage device (such as a floppy disk or USB flash disk) as the permanent storage device. Like the permanent storage device 1435, the system memory 1425 is a read-and-write memory device. However, unlike storage device 1435, the system memory is a volatile read-and-write memory, such a random access memory. The system memory stores some of the instructions and data that the processor needs at runtime. In some embodiments, the invention's processes are stored in the system memory 1425, the permanent storage device 1435, and/or the read-only memory 1430.

The bus 1405 also connects to the input and output devices 1440 and 1445. The input devices enable the user to communicate information and select commands to the computer system. The input devices 1440 include alphanumeric keyboards and pointing devices. The output devices 1445 display images generated by the computer system. For instance, these devices display a graphical user interface. The output devices include printers and display devices, such as cathode ray tubes (CRT) or liquid crystal displays (LCD).

Finally, as shown in FIG. 14, bus 1405 also couples computer 1400 to a network 1465 through a network adapter (not shown). In this manner, the computer can be a part of a network of computers (such as a local area network ("LAN"), a wide area network ("WAN"), or an Intranet), or a network of networks, such as the internet. For example, the computer 1400 may be coupled to a web server (network 1465) so that a web browser executing on the computer 1400 can interact with the web server as a user interacts with a graphical user interface that operates in the web browser.

Any or all components of computer system 1400 may be used in conjunction with the invention. For instance, each of the computer readable memories of the computer system 1400 may function as the storage solution for some embodiments of the invention. Similarly, each of the computer readable memories may store the processes and dissemination scripts for implementing the various metadata tagging and data dissemination functionalities. One of ordinary skill in the art would appreciate that any other system configuration may also be used in conjunction with the present invention.

While the invention has been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

We claim:

1. A method comprising:
    a) receiving medically related data via software executing on a computing processor from at least one medical data source in an automated manner, said data comprising a plurality of data components;
    b) organizing the plurality of data components, in an automated manner via software executing on a computing processor, into different subsets of the data components, wherein a plurality of the subsets of the data components comprise only a portion of the received data components but not all of the data components; and
    c) disseminating the different sets of the data components to a plurality of medical care providing members via software executing on a computing processor to facilitate operations performed by said members, wherein disseminating involves a plurality of dissemination scripts, each dissemination script defining rules for determining the relevancy of said data to said members;
    wherein disseminating involves the steps of:
    d) automatically pre-populating clinical notes of the plurality of medical care providing members with the data components related to patients under the care of the medical care providing members;

e) identifying data components that are relevant to the purposes of the medical care providing members and supplying the relevant data components identified for each particular medical care providing member to the particular medical care providing member; and f) sending the pre-populated clinical notes to an electronic device of each particular medical care providing member.

2. The method of claim 1, wherein a medical care providing member is a physician of a hospital.

3. The method of claim 1, wherein the step of receiving the medically related data comprises aggregating the medically related data from a plurality of medical data sources into a particular data item, each medical data source supplying a set of the received data components for the particular data item.

4. The method of claim 3, wherein disseminating the different sets of the data components comprises identifying data components of the particular data item that are relevant to the purposes of each member and supplying the relevant data components identified for each particular member from the particular data item to the particular member.

5. The method of claim 1 further comprising verifying completeness of said data prior to dissemination.

6. The method of claim 5 further comprising notifying at least one data source to provide additional data to complete said data when said data is incomplete.

7. The method of claim 6 wherein notifying the at least one data source comprises dynamically generating an editable form to send to the at least one data source, wherein said data form comprises data fields to specify incomplete data components.

8. The method of claim 6 wherein notifying the at least one data source comprises modifying a user interface of the at least one data source in order to specify data fields for incomplete data components.

9. The method of claim 1, wherein operations performed by a first member are different from operations performed by a second member and a first set of data components to disseminate to the first member is different than a second set of data components to disseminate to the second member.

10. The method of claim 1, wherein the medically related data comprises objective medical data and subjective medical data.

11. The method of claim 10, wherein the objective medical data comprises vital statistics and laboratory results provided by various electronic monitors monitoring a patient.

12. The method of claim 1, wherein disseminating the sets of data components comprises wirelessly transmitting said sets of data components to the plurality of medical care providing members.

13. The method of claim 1 further comprising storing said medically related data within a non-transitory data storage, wherein disseminating different sets of the data components comprises processing the medically related data stored in the non-transitory data storage.

14. A method comprising:
a) receiving medically related data via software executing on a computing processor for a particular patient from a medical data source, said medical data comprising a plurality of data components;
b) processing the medical data, in an automated manner via software executing on a computing processor, to identify a plurality of subsets of the data components relevant to a plurality of medical care providing members;
c) disseminating the different sets of the data components to the plurality of medical care providing members via software executing on a computing processor to facilitate operations performed by said members, wherein disseminating involves a plurality of dissemination scripts, each dissemination script defining rules for determining the relevancy of said data to said of members;

wherein disseminating involves the steps of:
d) automatically pre-populating clinical notes of the plurality of medical care providing members with the data components related to the particular patient;
e) identifying data components that are relevant to the purposes of each of the medical care providing members and supplying the relevant data components identified for each particular medical care providing member to the particular medical care providing member; and
f) sending the pre-populated clinical notes to an electronic device of each particular medical care providing member.

15. The method of claim 14, wherein the processing of the medical data comprises identifying data components relevant to the different members based on different functionalities performed by each of the members.

16. The method of claim 14, wherein the processing of the medical data comprises identifying values of data components that are within a set of threshold values as relevant data components to disseminate.

17. The method of claim 14 further comprising organizing the different sets of data components prior to providing the data components to the members such that data components most relevant to functionalities of the member are presented first.

18. The method of claim 14, wherein processing the medical data occurs according to the rules of the dissemination script.

19. The method of claim 14, wherein the different sets of data components comprise at least one shared data component.

20. The method of claim 14, wherein the processing of the medical data comprises determining whether the received data is complete.

21. The method of claim 20 further comprising sending an electronic data acquisition form for acquiring additional data to at least one particular medical data source prior to providing the different the different sets of data components when the received data is incomplete.

22. The method of claim 21, wherein the electronic data acquisition form is dynamically created to cure the incomplete data from the particular medical data source.

23. The method of claim 14, wherein receiving the medical data comprises automatically aggregating medical data from a plurality of medical data sources.

24. The method of claim 23, wherein the plurality of medical data sources comprise a plurality of healthcare monitoring devices, each device for monitoring different healthcare specific parameters.

25. The method of claim 14, wherein the plurality of members comprise different databases of a medical care provider.

26. The method of claim 25, wherein the different databases comprises a quality reporting database, a research database, and a billing database.

27. A method comprising:
a) receiving medical data via software executing on a computing processor from at least one medical data source, said data comprising a plurality of data components;

b) tagging, in an automated manner via software executing on a computing processor, each data component of the medical data with identification information including metadata tags;

c) indentifying via software executing on a computing processor, based on said tags associated with the data components, a plurality of subsets of the data components relevant to different members of a medical care provider; and d) distributing via software executing on a computing processor said subsets of the data components to a plurality of members based on the tags associated with the data components, wherein the tags specify access permissions to the data components by the plurality of members.

28. The method of claim 27, wherein the identification information associated with the tags specifies a source of the received data and a timestamp indicating when the data was received.

29. A system comprising:

a data aggregator for aggregating medically related data from a plurality of medical data sources in an automated manner via software executing on a computing processor, said data comprising a plurality of data components;

a dissemination engine for identifying via software executing on a computing processor, in an automated manner, a plurality of subsets of the data components relevant to different members of a medical care provider and for disseminating the subsets of the data components to said members to facilitate operations performed by said members, wherein said dissemination engine defines rules for determining the relevancy of the data components;

wherein said dissemination engine automatically pre-populates clinical notes of a plurality of medical care providing members with the data components related to patients under the care of the medical care providing members, identifies data components that are relevant to the purposes of the medical care providing member and supplying the relevant data components identified for each particular medical care providing member from to the particular medical care providing member and sends the pre-populated clinical notes to an electronic device of each particular medical care providing member.

* * * * *

UNITED STATES PATENT AND TRADEMARK OFFICE
CERTIFICATE OF CORRECTION

| | | |
|---|---|---|
| PATENT NO. | : 8,805,703 B2 | Page 1 of 1 |
| APPLICATION NO. | : 12/247987 | |
| DATED | : August 12, 2014 | |
| INVENTOR(S) | : Martin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1040 days.

Signed and Sealed this
Eleventh Day of August, 2015

Michelle K. Lee
*Director of the United States Patent and Trademark Office*